(12) United States Patent
Imai et al.

(10) Patent No.: US 6,245,911 B1
(45) Date of Patent: Jun. 12, 2001

(54) DONEPEZIL POLYCRYSTALS AND PROCESS FOR PRODUCING THE SAME

(75) Inventors: Akio Imai; Toshiyuki Ichinohe; Takashi Endo; Tomio Tsurugi; Makoto Uemura, all of Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/555,807

(22) PCT Filed: Dec. 1, 1998

(86) PCT No.: PCT/JP98/05405

§ 371 Date: Jun. 5, 2000

§ 102(e) Date: Jun. 5, 2000

(87) PCT Pub. No.: WO99/29668

PCT Pub. Date: Jun. 17, 1999

(30) Foreign Application Priority Data

Dec. 5, 1997 (JP) .................................................. 9-336165

(51) Int. Cl.[7] .................................................. C07D 211/06
(52) U.S. Cl. .................................................. 546/206
(58) Field of Search .............................................. 546/206

(56) References Cited

U.S. PATENT DOCUMENTS 5,985,864 * 11/1999 Imai et al. .......................... 514/212

FOREIGN PATENT DOCUMENTS

| 179151 | 3/1989 | (JP) . |
| 1053576 | 2/1998 | (JP) . |
| A1-9746527 | 12/1997 | (WO) . |

OTHER PUBLICATIONS

Kryger et al, J. Physiol. Paris, vol. 92, # 3–4, pp. 191–194, Jun. 1998.*

Kawakami et al, Bioorg. Med. Chem., vol. 4, # 9, pp. 1429–1446, Sep. 1996.*

* cited by examiner

*Primary Examiner*—James H. Reamer
(74) *Attorney, Agent, or Firm*—Birch, Stewart, Kolasch & Birch, LLP

(57) ABSTRACT

The present invention provides novel polymorphic crystals (A) to (C) having excellent handling properties and an extremely low content of residual solvent of donepezil used as a precursor for production of donepezil hydrochloride having an excellent action as a medicament, and an industrial process for producing the same. Further, the novel polymorphic crystals (A) to (C) according to the present invention are characterized by the powder X-ray diffraction pattern and/or IR absorption peaks of donepezil represented by the following formula:

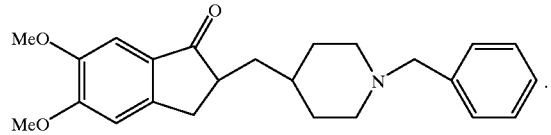

21 Claims, 12 Drawing Sheets

DONEPEZIL POLYCRYSTALS AND PROCESS FOR PRODUCING THE SAME

This application is the national phase under 35 U.S.C. §371 of PCT International Application No. PCT/JP98/05405 which has an International filing date of Dec. 1, 1998, which designated the United States of America.

FIELD OF THE INVENTION

The present invention relates to novel polymorphic crystals (A) to (C) of donepezil (1-benzyl-4-[(5,6-dimethoxy-1-indanone)-2-yl]methylpiperidine, free compound) as a precursor for production of donepezil hydrochloride (chemical name: 1-benzyl-4-[(5,6-dimethoxy-1-indanone)-2-yl] methylpiperidine hydrochloride) having an excellent action as a medicament disclosed in Example 4 of JP-A 64-79151 (EP-A 296560, U.S. Pat. No. 4,895,841), specifically as a prophylactic and therapeutic agent for senile dementia, and in particular as a prophylactic and therapeutic agent for Alzheimer's disease, and an industrial process for producing the same.

Hereinafter, polymorphic crystals (A) to (C) are referred to as types (A) to (C), respectively.

PRIOR ART

Donepezil hydrochloride is a therapeutic agent having an inhibitory action on acetylcholinesterase for treating a variety of senile dementia, is particularly useful as a prophylactic, therapeutic and ameliorating agent for Alzheimer-type senile dementia and is on the market or under development in all the countries of the world.

Donepezil hydrochloride is produced by first producing donepezil which is a free compound and then converting it into a hydrochloride. On the one hand, donepezil is, in itself, an excellent medicament but is also used as a precursor for production of donepezil hydrochloride.

Accordingly, donepezil preferably has such physical properties as to allow it to occur in the form of crystals not being sticky but being dry in order to achieve excellent filtering properties after crystallization and to facilitate recovery of its filter cake by scraping. However, crystals of donepezil excellent in handling properties is not known so far. Further, the presence of polymorphic crystals of donepezil is not known.

In a method described in Example 4 of JP-A 64-79151, a crude donepezil product was purified by column chromatography, and residues obtained by concentrating desired fractions were immediately converted into a hydrochloride. Accordingly, donepezil has not been obtained as crystals.

However, it goes without saying that donepezil in the form crystals not being sticky but being dry is preferable because of excellent filtering properties, easy scraping and handling.

Further, in the prior art, the desired compound is purified by column chromatography (methylene chloride system), but purification by column chromatography requires a large amount of solvent and the column is discarded after use, and is thus very disadvantageous in production cost. In addition, the used solvent is evaporated in a large amount into the atmosphere, and therefore, the column chromatography is preferably not used if possible from the viewpoint of working environment or environmental protection.

Further, because donepezil according to the present invention is a raw material of a medicament, the solvent remaining therein should be as low as possible and simultaneously be an uninfluential solvent in order to prevent its unpleasant effect on the human body.

DISCLOSURE OF THE INVENTION

The present inventors extensively studied to improve the problems described above. As a result, they found that the novel polymorphic crystals (A) to (C) of donepezil described below are very dry, can be purified without using column chromatography and have a very low content of residual solvent, and therefore these crystals are a very preferable raw material as a medicament, thus completing the present invention.

That is, the present invention provides three kinds of novel polymorphic crystals (A) to (C) of donepezil which are capable of purification without using column chromatography, are dry and thus excellent in handling properties, and have an extremely low content of residual solvent, and an industrial process for producing the same.

The present invention specifically relates to the novel polymorphic crystals (A) to (C) of donepezil represented by the following formula:

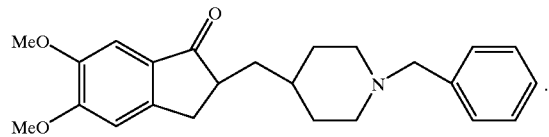

which are characterized by a powder X-ray diffraction pattern and/or IR absorption peaks in potassium bromide.

Measurement Method and Condition, for Powder X-ray Diffraction Pattern (1) Measurement Method About 100 mg sample was measured for its powder X-ray diffraction pattern under the following conditions.

(2) Measurement Conditions

Target: Cu
Filter: monochro
Voltage: 40 KV
Current: 20 mA
Slit: DS 1, RS 0.15, SS 1
Scan speed: 2 deg/min.

Range: 5–30°
Wave length: 1.5406 A
Sampling width: 0.020 deg.

Measurement Method and Condition for Infrared Absorption Spectrum

Measured by FT-IR (SCAN: 4 scans, 4.0 cm$^{-1}$, abex) according to the Japanese Pharmacopoeia, general test methods, infrared absorption spectrum, potassium bromide tablet method.

Figure 1:
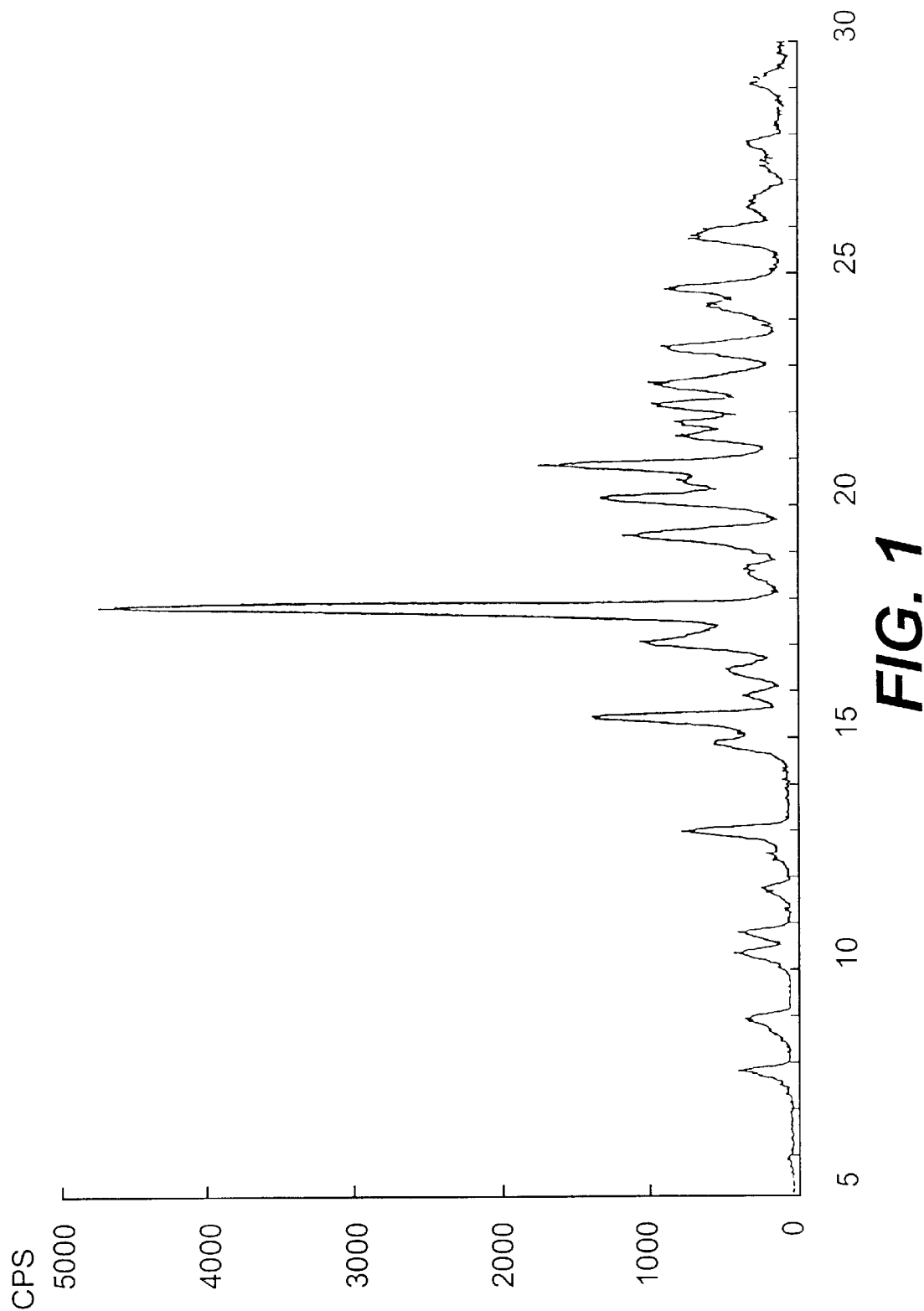
FIG. 1 shows a powder X-ray diffraction pattern of type A donepezil crystals.

(1) Type A Crystals
Peaks in powder X-ray diffraction pattern (see FIG. 1):

| Diffraction angle (2θ, °) | Intensity (I/I$_O$) |
|---|---|
| 7.68 | 8 |
| 8.52 | 4 |
| 8.80 | 7 |
| 10.20 | 8 |
| 10.64 | 8 |
| 11.60 | 5 |
| 12.86 | 16 |
| 14.80 | 12 |
| 15.34 | 30 |
| 15.82 | 8 |
| 16.34 | 10 |
| 16.96 | 22 |
| 17.66 | 100 |
| 19.26 | 24 |
| 20.08 | 29 |
| 20.46 | 17 |
| 20.82 | 35 |
| 21.46 | 17 |
| 21.76 | 17 |
| 22.14 | 21 |
| 22.60 | 21 |
| 23.38 | 20 |
| 24.28 | 14 |
| 24.66 | 19 |
| 25.78 | 16 |

Figure 7:
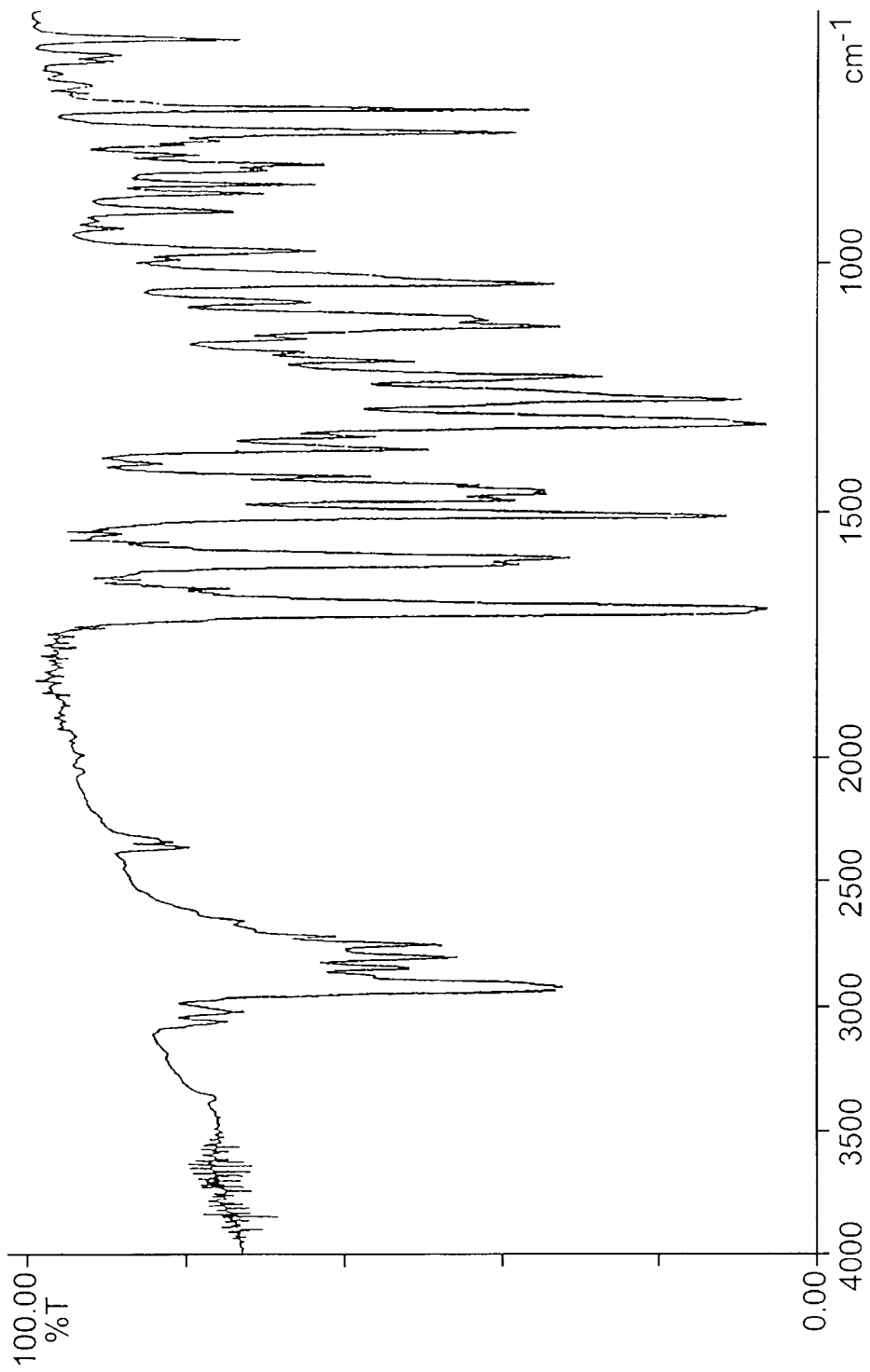
FIG. 7 shows an infrared absorption spectrum of type A donepezil crystals.

Peaks in infrared absorption spectrum in potassium bromide (see FIG. 7):
Wave length: 561.3, 699.8, 743.1, 803.1, 841.3, 858.4, 893.8, 972.5, 1035.7, 1074.7, 1122.9, 1191.8, 1220.3, 1262.4, 1311.8, 1365.6, 1420.5, 1456.6, 1501.3, 158.9.0, 1690.1, 2799.6, 2919.1 cm$^{-1}$.

Figure 2:
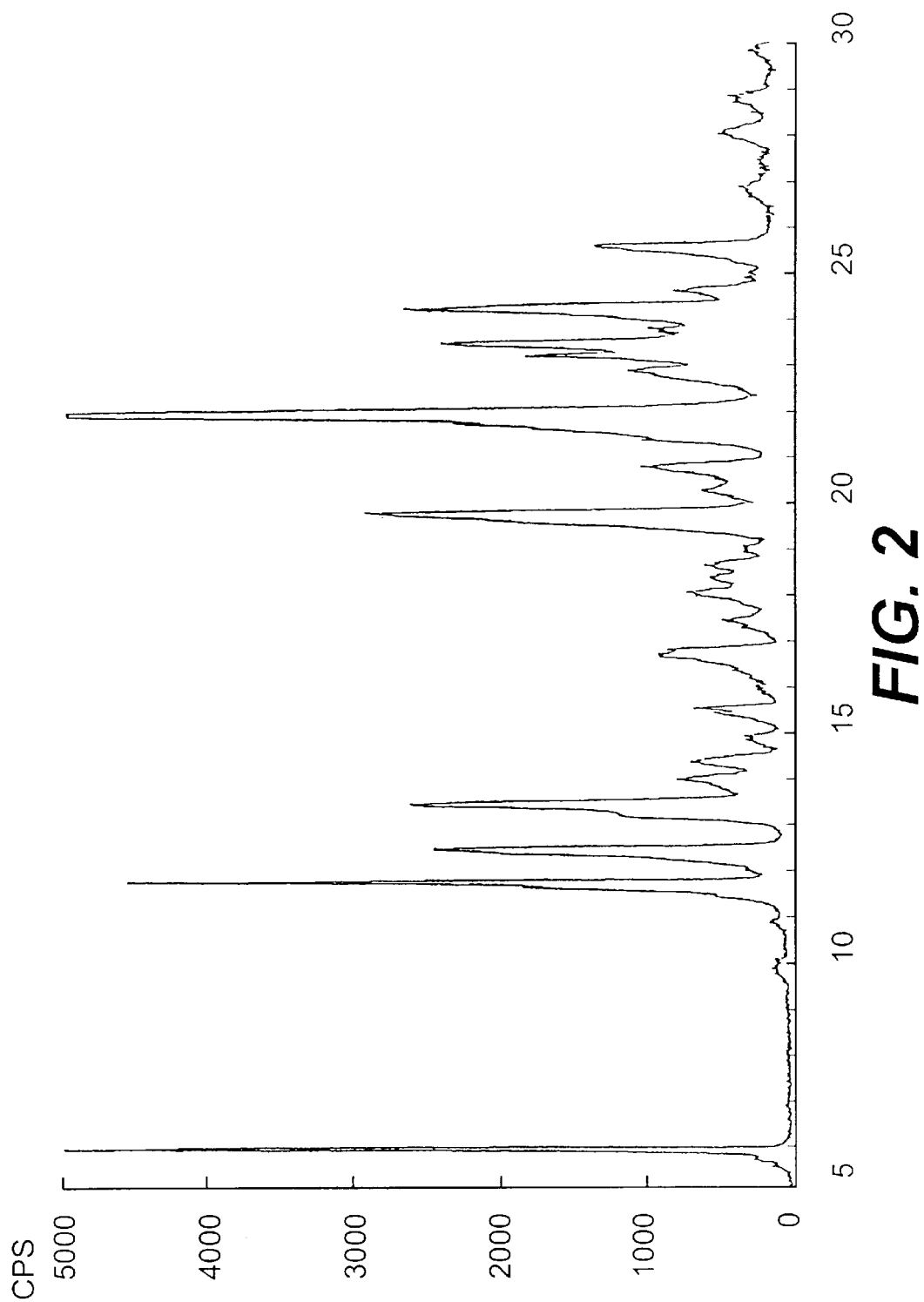
FIG. 2 shows a powder X-ray diffraction pattern of type B donepezil crystals.

(2) Type B Crystals
Peaks in powder X-ray diffraction pattern (see FIG. 2):

| Diffraction angle (2θ, °) | Intensity (I/I$_O$) |
|---|---|
| 5.82 | 79 |
| 11.28 | 8 |
| 11.46 | 26 |
| 11.58 | 60 |
| 11.86 | 5 |
| 12.04 | 10 |
| 12.30 | 36 |
| 13.02 | 17 |
| 13.30 | 38 |
| 13.66 | 7 |
| 13.88 | 11 |
| 14.40 | 6 |
| 15.34 | 8 |
| 15.46 | 10 |
| 16.46 | 9 |
| 16.60 | 14 |
| 16.74 | 13 |
| 18.00 | 11 |
| 18.30 | 8 |
| 18.56 | 9 |
| 19.34 | 12 |
| 19.48 | 26 |
| 19.70 | 42 |
| 20.24 | 9 |
| 20.76 | 15 |
| 21.34 | 14 |
| 21.58 | 24 |
| 21.72 | 33 |
| 21.90 | 100 |
| 22.76 | 13 |
| 22.90 | 16 |
| 23.22 | 26 |
| 23.48 | 35 |
| 23.82 | 14 |
| 24.04 | 17 |
| 24.22 | 38 |
| 24.52 | 8 |
| 24.66 | 12 |
| 25.60 | 20 |
| 28.04 | 7 |

Figure 8:
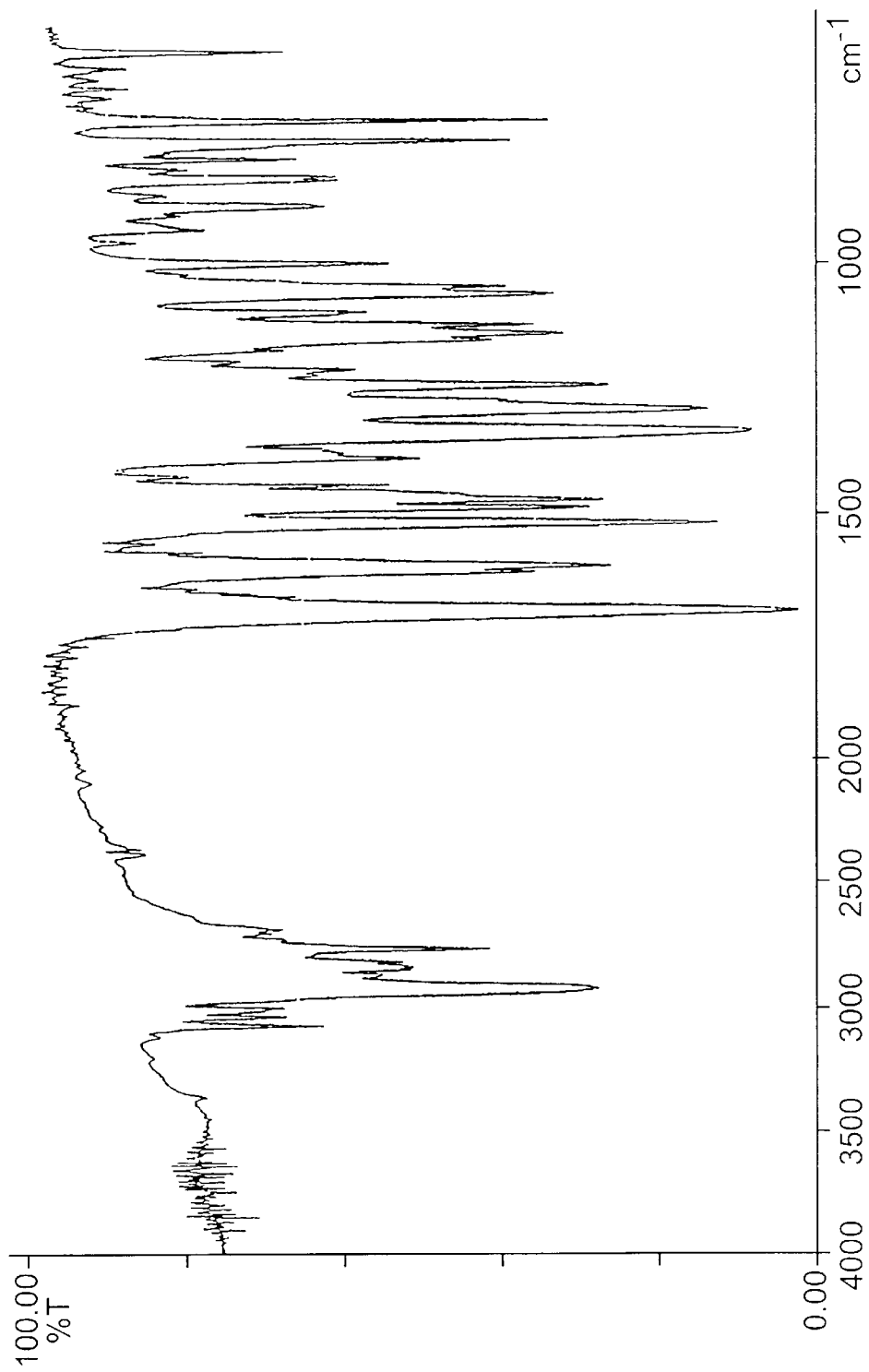
FIG. 8 shows an infrared absorption spectrum of type B donepezil crystals.

Peaks in infrared absorption spectrum in potassium bromide (see FIG. 8):
Wave length: 561.7, 697.5, 738.0, 770.0, 809.6, 861.9, 976.0, 1037.8, 1073.8, 1119.7, 1221.4, 1266.3, 1308.4, 1365.0, 1420.4, 1453.9, 1468.9, 1500.0, 1591.7, 1685.7, 2761.3, 2922.2, 3029.5, 3067.7 cm$^{-1}$.

Figure 3:
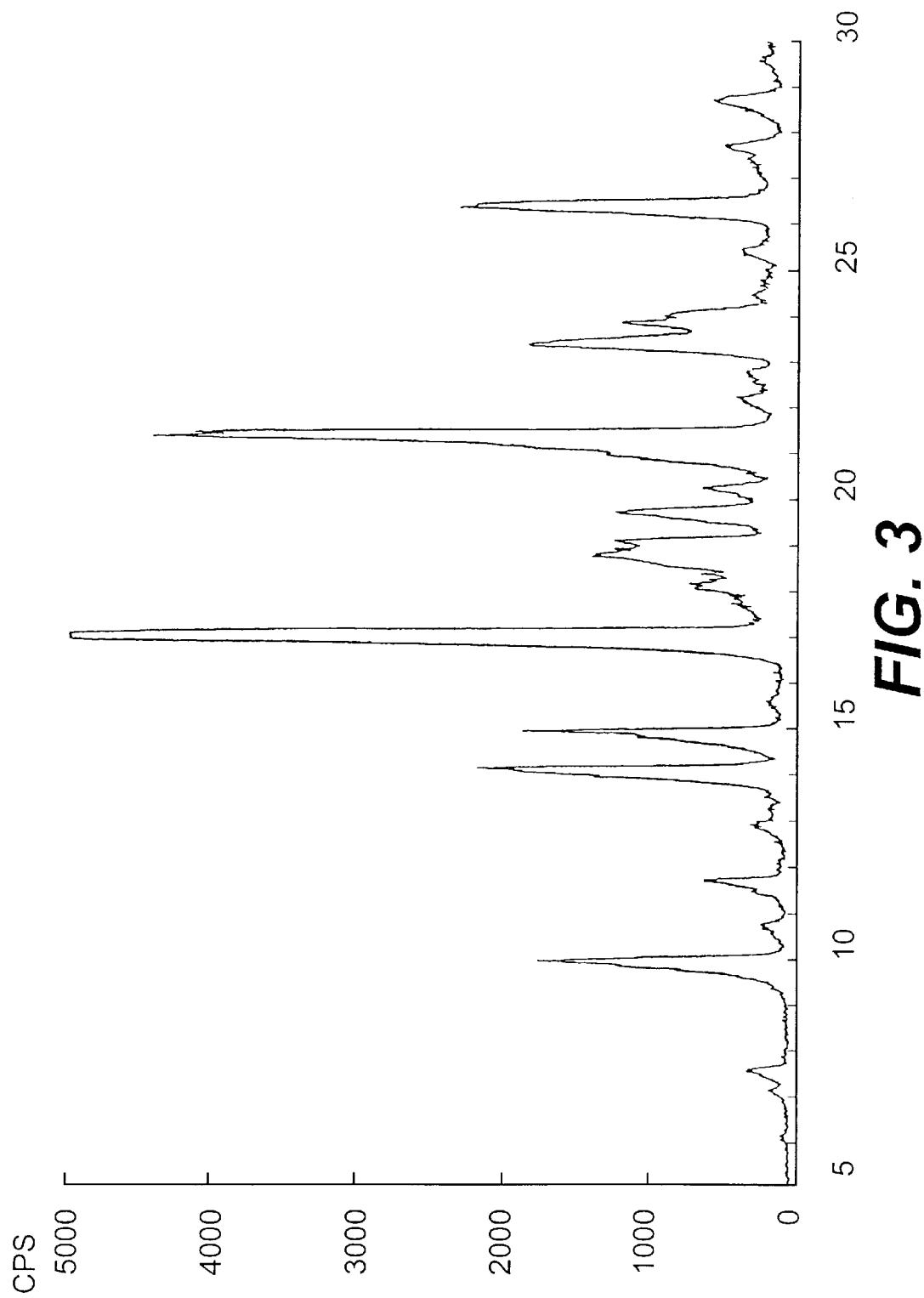
FIG. 3 shows a powder X-ray diffraction pattern of type C donepezil crystals.

(3) Type C Crystals
Peaks in powder X-ray diffraction pattern (see FIG. 3):

| Diffraction angle (2θ, °) | Intensity (I/I$_O$) |
|---|---|
| 7.42 | 3 |
| 7.56 | 4 |
| 9.60 | 4 |
| 9.74 | 10 |
| 9.82 | 15 |
| 9.94 | 23 |
| 11.46 | 4 |
| 11.58 | 6 |
| 11.58 | 9 |
| 13.78 | 8 |
| 13.90 | 9 |
| 14.78 | 14 |
| 14.94 | 25 |
| 17.00 | 100 |
| 17.18 | 46 |
| 18.12 | 10 |
| 18.22 | 10 |
| 18.44 | 8 |
| 18.60 | 12 |
| 18.84 | 19 |
| 18.98 | 17 |
| 19.12 | 17 |
| 19.76 | 17 |
| 20.30 | 9 |
| 20.86 | 13 |
| 21.00 | 18 |
| 21.14 | 25 |
| 21.50 | 48 |
| 23.44 | 26 |
| 23.92 | 17 |
| 24.20 | 10 |
| 26.22 | 13 |
| 26.54 | 25 |
| 27.74 | 7 |
| 28.80 | 7 |

Figure 9:
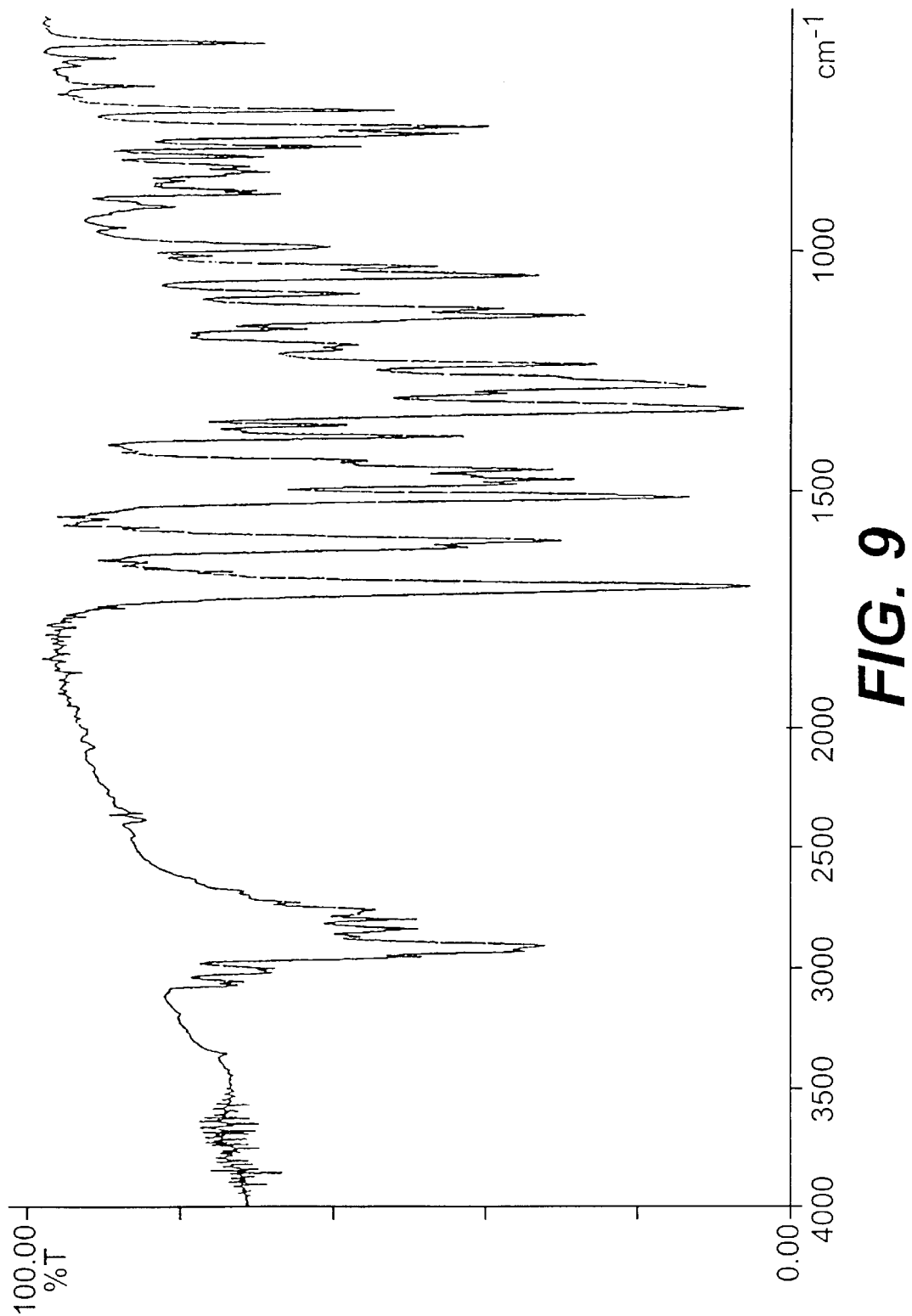
FIG. 9 shows an infrared absorption spectrum of type C donepezil crystals.

Peaks in infrared absorption spectrum in potassium bromide (see FIG. 9):
Wave length: 559.8, 648.4, 698.7, 733.5, 746.2, 768.1, 787.2, 818.8, 863.7, 974.0, 1036.4, 1073.0, 1122.1, 1221.3, 1263.0, 1310.3, 1342.3, 1367.5, 1438.1, 1459.1, 1498.6, 1591.9, 1688.1, 2909.3 cm$^{-1}$.

Figure 4:
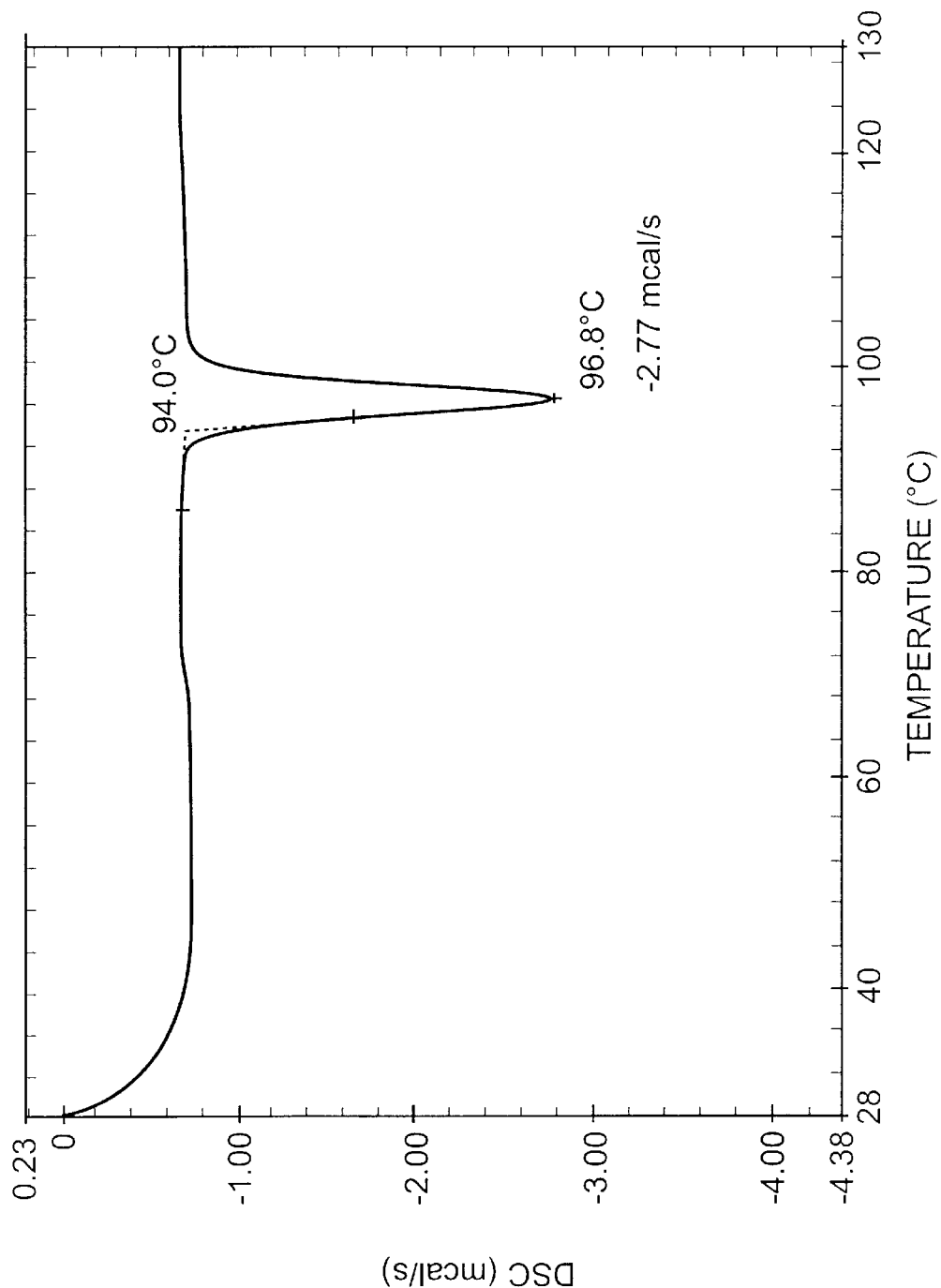
FIG. 4 shows the result of differential scanning calorimetry (DSC) of type A donepezil crystals.
Figure 5:
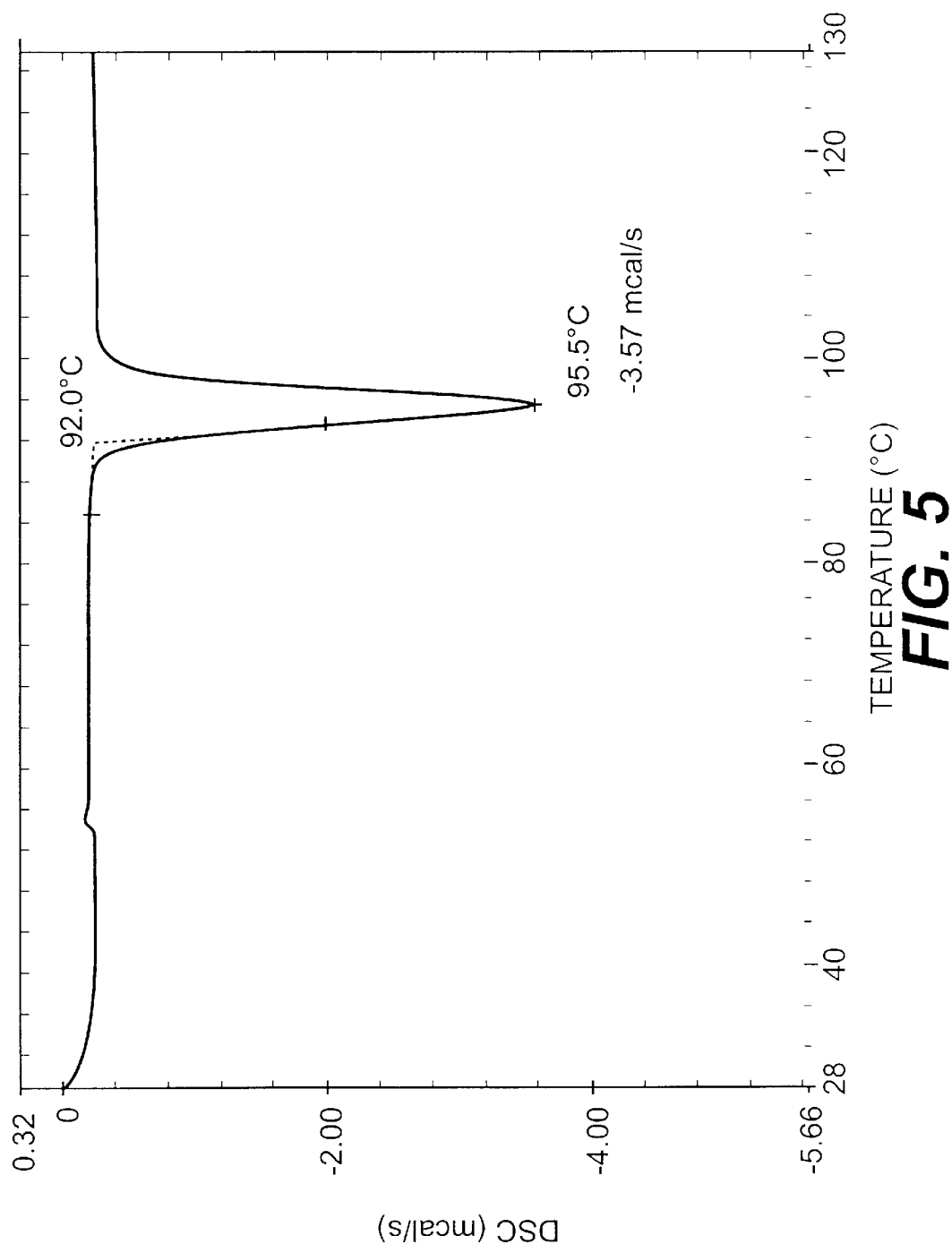
FIG. 5 shows the result of differential scanning calorimetry (DSC) of type B donepezil crystals.
Figure 6:
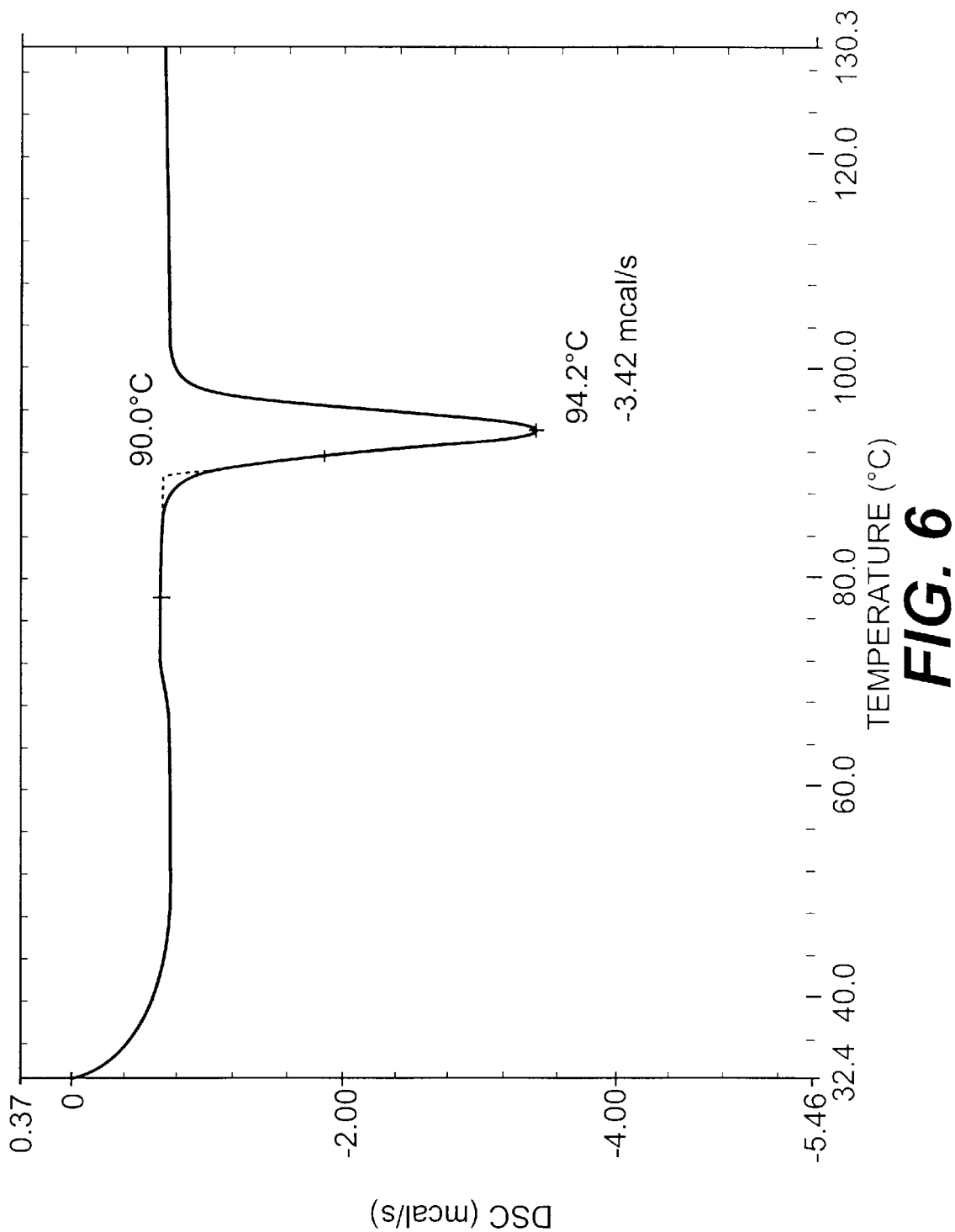
FIG. 6 shows the result of differential scanning calorimetry (DSC) of type C donepezil crystals.

Novel crystals (A) to (C) of donepezil according to the present invention also give different results in differential scanning calorimetry (DSC) under the following conditions and have crystal forms completely different from each other (see FIGS. 4 to 6).

Measurement Method and Conditions for Differential Scanning Calorimetry (DSC)

About 3 to 6 mg sample was weighed. The amount of the sample was 2.0820 mg for type A, 5.660 mg for type B and 4.540 mg for type C, respectively. Thermal analysis was conducted under the following conditions:

Reference: empty
Scan speed: 10° C./min.
Sampling: 1.0 sec.
Upper limit: 130° C.
Lower limit: Room temperature
Thermocouple: PL Hereinafter, a process for producing these novel crystals of donepezil is specifically described.

Donepezil in the present invention refers to a free compound of donepezil hydrochloride described in Example 4 of JP-A 64-79151, that is, 1-benzyl-4-[(5,6-dimethoxy-1-indanone)-2-yl]methylpiperidine.

The novel crystals (A) to (C) of donepezil according to the present invention can be obtained by the conventional crystallization procedures, but to achieve any of the crystals certainly, seed crystals in a desired crystal form are preferably added for crystallization. Here, the seed crystals mean a very small amount of crystals of known crystal form.

(1) Type A Crystals 1-1) A solution of donepezil/methanol-denatured ethanol is crystallized at 10° C. or less within 20 hours (see Example 1).

1-2) Seed crystals of type A are added to a donepezil solution which is then crystallized at 20° C. or less within 1 hour (see Example 2).

1-3) Donepezil is dissolved in methanol-denatured ethanol, and then seed crystals of type A are added to crystallize under cooling (see Example 17).

(2) Type B Crystals 2-1) A solution of donepezil/THF is concentrated (see Example 3).

2-2) A solution of donepezil/methanol-denatured ethanol is crystallized at 10° C. or less for 20 hours or more (see Example 4).

2-3) Seed crystals of type B are added to a donepezil solution which is then cooled at 15° C. or less and crystallized at 20 to 30° C. within 2 hours (see Example 5).

2-4) Seed crystals of type B are added to a donepezil solution which is then crystallized at 15° C. or less within 1 hour (see Example 6).

2-5) Donepezil is dissolved in methanol-denatured ethanol, and then seed crystals of type B are added to crystallize under cooling (see Example 18).

(3) Type C Crystals 3-1) A solution of donepezil/methanol-denatured ethanol is cooled to 10° C. or less, and after crystal precipitation, it is heated to 20° C. or more and then cooled to 10° C. or less to crystallize (see Example 7).

3-2) A solution of donepezil/methanol-denatured ethanol is cooled, and after crystal precipitation, it is crystallized at 15 to 25° C. (see Example 8).

3-3) Donepezil/methanol-denatured ethanol is gradually cooled (see Example 9).

3-4) Seed crystals of type C are added to a donepezil solution and the resulting mixture is cooled to 15° C. or less, then crystallized at 25 to 35° C. for 2 hours or more, and further crystallized at 15° C. or less (see Examples 10 to 13).

3-5) Donepezil and seed crystals of type C are suspended in a solvent at 20 to 40° C. (see Examples 14 to 16).

3-6) Donepezil is dissolved in methanol-denatured ethanol, and then seed crystals of type C are added to crystallize in a warm water bath (see Example 19).

3-7) Donepezil is dissolved in methanol, and then seed crystals of type C are added to crystallize in a warm water bath (see Example 20).

3-8) Donepezil is dissolved in ethanol, and then seed crystals of type C are added to crystallize in a warm water bath (see Example 21).

3-9) Donepezil is dissolved in isopropanol, and then seed crystals of type C are added to crystallize in a warm water bath (see Example 22).

3-10) Donepezil is dissolved in acetone, and then seed crystals of type C are added to crystallize at room temperature (see Example 23).

3-11) Donepezil is dissolved in methyl ethyl ketone, and then seed crystals of type C are added to crystallize at room temperature (see Example 24).

3-12) Donepezil is dissolved in methyl isobutyl ketone, and then seed crystals of type C are added to crystallize at room temperature (see Example 25).

3-13) Donepezil is dissolved in toluene-denatured ethanol, and then seed crystals of type C are added to crystallize in a warm water bath (see Examples 26 and 27).

3-14) Donepezil is dissolved in 2-ethoxyethanol, and then seed crystals of type C are added to crystallize in a warm water bath (see Example 28).

3-15) Donepezil is dissolved in THF, and then seed crystals of type C are added to crystallize under cooling (see Example 29).

3-16) Donepezil is dissolved in 1,4-dioxane, and then seed crystals of type C are added to crystallize at room temperature (see Example 30).

3-17) Donepezil is dissolved in 1,3-dioxolane, and then seed crystals of type C are added to crystallize under cooling (see Example 31).

3-18) Donepezil is dissolved in 1,2-dimethoxyethane, and then seed crystals of type C are added to crystallize under cooling (see Example 32).

3-19) Donepezil is dissolved in methyl acetate, and then seed crystals of type C are added to crystallize under cooling (see Example 33).

3-20) Donepezil is dissolved in ethyl acetate, and then seed crystals of type C are added to crystallize in a warm water bath (see Examples 34 and 35).

3-21) Donepezil is dissolved in isopropyl acetate, and then seed crystals of type C are added to crystallize in a warm water bath (see Example 36).

3-22) Donepezil is dissolved in acetonitrile, and then seed crystals of type C are added to crystallize under cooling (see Example 37).

3-23) Donepezil is dissolved in ethyl benzene, and then seed crystals of type C are added to crystallize at room temperature (see Example 38).

3-24) Donepezil is dissolved in cyclohexane, and then seed crystals of type C are added to crystallize in a warm water bath (see Example 39).

3-25) Donepezil is dissolved in diethyl ether, and then seed crystals of type C are added to crystallize at room temperature (see Example 40).

3-26) Donepezil is dissolved in methanol and water, and then seed crystals of type C are added to crystallize at room temperature (see Example 41).

3-27) Donepezil is dissolved in acetonitrile and water, and then seed crystals of type C are added to crystallize under cooling (see Examples 42 and 43).

3-28) Donepezil is dissolved in acetone and hexane, and then seed crystals of type C are added to crystallize at room temperature (see Example 44).

The crystallization solvents in the processes 1-2), 2-3), 2-4), 3-4) and 3-5) described above are not limited, and any solvents in which donepezil is soluble more or less, or a mixture of such solvents, can be used. However, preferable examples include lower alcohols, specifically methanol, ethanol, n-propanol, i-propanol, methanol-denatured ethanol etc.

The amount of the solvent used is not also limited and is varied depending on the type of solvent, lot size etc. Generally, it is used, per g of donepezil, in an amount of 1 to 100 ml, preferably 2 to 50 ml, more preferably 3 to 10 ml.

The operation conditions other than described above, for example the presence or absence of stirring, are not also limited, and crystallization may be conducted with or without stirring. The crystallization temperature is not limited either, but good results can be obtained by conducting crystallization usually at a temperature of an ice-cold water bath to a room temperature to warm water bath. Addition of seed crystals is also arbitrary, but upon addition thereof, the desired polymorphic crystals can be certainly obtained in a shorter time. The crystallization time is also varied depending on these operation conditions, but may be usually 30 min. to 24 hours or so.

The precipitated crystals can be collected by a usual filtration method such as gravity filtration, filtration under suction (under reduced pressure), centrifugation etc. The novel polymorphic crystals (A) to (C) according to the present invention are dry and can thus be collected very easily in a shorter time, thus exhibiting excellent physical properties in handling and production efficiency.

The crystals thus collected by filtration can be made completely free of residual solvent certainly and easily by a usual drying method such as spontaneous drying, drying under reduced pressure (in vacuo), heating drying, heating drying under reduced pressure, etc.

As the effect of the present invention, there can be obtained crystals of donepezil which are preferable and excellent in handling properties, that is, not being sticky but being dry, excellent in filtering properties after crystallization and capable of easily recovering its filter cake by scraping.

Although any novel crystals (A) to (C) of donepezil according to the present invention have excellent handling properties, type C is particularly excellent in handling property, and type A and B follow in this order.

Further, as compared with a product in the prior art (purification by column chromatography), the novel crystals (A) to (C) of donepezil according to the present invention have a significantly low content of residual solvent and free of highly toxic methylene chloride, and are thus a very preferable raw medicine as a medicament.

Hereinafter, the present invention is described more in detail by reference to Examples and Comparative Examples, which however are not intended to limit the present invention.

EXAMPLES

Examples 1, 2 and 17

Production of Polymorphic Crystal (A) of Donepezil

Examples 3 to 6 and 18

Production of Polymorphic Crystal (B) of Donepezil

Examples 7 to 16 and 19 to 44

Production of Polymorphic Crystal (C) of Donepezil

Comparative Examples 1 to 3

Production of Donepezil
(Purification by Column Chromatography)

Donepezil used in Examples was produced according to Example 4 of JP-A 64-79151. $^1$H-NMR(400 MHz, CD$_3$OD, 30° C.); δ(ppm) 1.33(3H,m), 1.55(1,m), 1.72(1H,m), 1.83 (2H,m), 2.05(2H,m), 2.72(2H,m), 2.94(2H,m), 3.27(1H, dd, J=18, 8 Hz), 3.54(2H,s), 3.86(3H,s), 3.95(3H,s), 7.04(1H,s), 7.14(1H,s), 7.30(1H,m), 7.35(4H,m).

Example 1

Production of Crystal Polymorphism of Donepezil
(Type A)

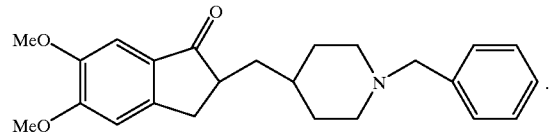

A solution of crude donepezil obtained by treating 1-benzyl-4-[(5,6-dimethoxy-1-indanone)-2-ylidenyl]methyl piperidine (92.7 g) obtained according to Example 3 of JP-A 64-79151 in the same manner as in Example 4 of the same publication in THF was concentrated. Methanol-denatured ethanol (649 ml) was added to the resulting residue, and the residue was dissolved under stirring. The solution was stirred for 17 hours at a bulk temperature of 10° C. or less in a cooling water bath (8° C.). The precipitated crystals were collected by filtration and washed with methanol-denatured ethanol (40 ml). The resulting crystals were dried (50° C.) to give 69.7 g of the title compound (yield, 74.8%).

By powder X-ray analysis, it was confirmed that the product was type A.

Example 2

Production of Crystal Polymorphism of Donepezil
(Type A)

200 g donepezil was weighed and placed in a 2 L four-necked round bottom flask, and 1200 ml methanol-denatured ethanol was added thereto. Then, the resulting mixture was heated under stirring in a water bath at 50° C. to dissolve. After dissolved (46° C.), the solution was ice-cooled, and type-A seed crystals (1 g) were added thereto at a bulk temperature of 30° C. After the mixture was stirred at a bulk temperature of 20° C. or less for 30 minutes, the precipitated crystals were filtered and washed with 120 ml methanol-denatured ethanol. The resulting crystals were dried for 3 hours with an air dryer at 50° C. to give 147.8 g of the title compound (yield, 73.9%).

By powder X-ray analysis, it was confirmed that the product was type A.

Example 3

Production of Crystal Polymorphism of Donepezil
(Type B)

A solution of crude donepezil obtained by treating 1-benzil- 4-[(5,6-dimethoxy-1-indanone)-2-ylidenyl]methyl piperidine (91.8 g) in the same manner as in Example 4 of the same publication in THF was concentrated to give 73.7 g of the title compound (yield, 79.9%).

By powder X-ray analysis, it was confirmed that the product was type B.

Example 4

Production of Crystal Polymorphism of Donepezil
(Type B)

A solution of crude donepezil obtained by treating 1-benzyl-4-[(5,6-dimethoxy-1-indanone)-2-ylidenyl]methyl piperidine (2.5 kg) in the same manner as in Example 4 of the same publication in THF was evaporated, to give residues. When the solvent was completely removed, the system was returned to ordinary pressure with nitrogen, methanol-denatured ethanol (120 L) was added thereto, and then the resulting mixture was stirred to dissolve. The resulting solution was stirred for 21 hours at a bulk temperature of 10° C. or less in a cooling water bath (8° C.). The precipitated crystals were filtered and washed with methanol-denatured ethanol (6.8 L). The resulting crystals were dried (50° C.) to give 12.7 kg of the title compound.

By powder X-ray analysis, it was confirmed that the product was type B.

Example 5

Production of Crystal Polymorphism of Donepezil
(Type B)

150 g donepezil was weighed and placed in a 2 L four-necked round bottom flask, and 900 ml methanol-denatured ethanol was added thereto. Then, the sample was dissolved by heating under stirring in a water bath at 50° C. After dissolved (44° C.), the solution was ice-cooled, and type-B seed crystals (1.5 g) were added thereto at a bulk temperature of 30° C. When the bulk temperature was decreased to 10° C., it was transferred to a water bath at 25° C. and stirred for 2 hours. Thereafter, it was ice-cooled, and the precipitated crystals were filtered. The resulting crystals were dried for 2 hours with an air dryer at 50° C. to give 123 g of the title compound (yield, 82%).

By powder X-ray analysis, it was confirmed that the product was type B.

Example 6

Production of Crystal Polymorphism of Donepezil
(Type B)

200 g donepezil was weighed and placed in a 2 L four-necked round bottom flask, and 1200 ml methanol-denatured ethanol was added thereto. Then, the sample was dissolved by heating under stirring in a water bath at 50° C. After dissolved (49° C.), the solution was ice-cooled, and type-B seed crystals (2 g) were added thereto at a bulk temperature of 28° C. After the mixture was stirred at a bulk temperature of 3 to 10° C. for 30 minutes, the precipitated crystals were collected by filtration. The resulting crystals were dried for 2 hours with an air dryer at 50° C. to give 174 g of the title compound (yield, 87%).

By powder X-ray analysis, it was confirmed that the product was type B.

Example 7

Production of Crystal Polymorphism of Donepezil
(Type C)

5.0 g donepezil was weighed and placed in a 50 ml four-necked round bottom flask, and 35 ml methanol-denatured ethanol was added thereto. Then, the sample was dissolved by heating under stirring in a water bath at 50° C. After the dissolution of the sample was confirmed (46° C.), the solution was ice-cooled. Crystals were precipitated at a bulk temperature of 3° C. and thereafter the mixture was transferred to a water bath at 25° C. and stirred for 8 hours. Thereafter, it was ice-cooled again and the precipitated crystals were collected by filtration and dried to give the title compound.

By powder X-ray analysis, it was confirmed that the product was type C.

Example 8

Production of Crystal Polymorphism of Donepezil
(Type C)

10 g donepezil was weighed and placed in a 200 ml three-necked round bottom flask, and 60 ml methanol-denatured ethanol was added thereto. Then, the sample was dissolved by heating under stirring in a water bath at 50° C. After the dissolution of the sample was confirmed (41° C.), the solution was cooled. Crystals were precipitated at a bulk temperature of 25° C. and thereafter the mixture was transferred to a water bath at 20° C. and stirred for 2 hours. The precipitated crystals were collected by filtration and dried to give the title compound.

By powder X-ray analysis, it was confirmed that the product was type C.

Example 9

Production of Crystal Polymorphism of Donepezil
(Type C)

10 g donepezil was weighed and placed in a 100 ml two-necked round bottom flask, and 60 ml methanol-denatured ethanol was added thereto. Then, the sample was dissolved by heating under stirring in a water bath at 50° C. After the dissolution of the sample was confirmed (43° C.), the solution was gradually cooled. Crystals were initiated to be precipitated at a bulk temperature of 22° C. The precipitated crystals were collected by filtration and dried to give the title compound.

By powder X-ray analysis, it was confirmed that the product was type C.

Example 10

Production of Crystal Polymorphism of Donepezil
(Type C)

76.8 g donepezil and 460 ml methanol-denatured ethanol were introduced into a 1 L four-necked round bottom flask, and the sample was dissolved by heating at 50° C. After the dissolution of the sample was confirmed (45.9° C.), the solution was cooled in a cooling water bath, and type-C seed crystals (0.4 g) were added thereto at a bulk temperature of 30° C. Crystals were precipitated at a bulk temperature of 18° C., and thereafter the mixture was transferred to a warm water bath (29° C.) and stirred for 15 hours. Thereafter, the mixture was transferred to a cooling water bath and stirred for 2 hours. The precipitated crystals were collected by filtration and washed with 60 ml methanol-denatured ethanol. The resulting crystals were dried to give 66.2 g of the title compound (yield, 86.2%)

By powder X-ray analysis, it was confirmed that the product was type C.

Example 11

Production of Crystal Polymorphism of Donepezil
(Type C)

20 g donepezil was weighed and placed in a 200 ml four-necked round bottom flask, and 120 ml methanol-denatured ethanol was added thereto. Then, the sample was dissolved by heating under stirring in a water bath at 50° C. After it was dissolved (45° C.), type-C seed crystals (100 mg) were added thereto at a bulk temperature of 30° C. After the mixture was stirred at a bulk temperature of 9 to 11° C. for 10 minutes, it was heated to a bulk temperature of 29° C. and stirred for 5 hours. Thereafter, the mixture was ice-cooled again, and after stirred at a bulk temperature of 9° C.

for 1 hour, the precipitated crystals were collected by filtration and washed with 12 ml methanol-denatured ethanol. The resulting crystals were dried for 2 hours with an air dryer at 50° C. to give 16.7 g of the title compound (yield, 83.5%).

By powder X-ray analysis, it was confirmed that the product was type C.

Example 12

Production of Crystal Polymorphism of Donepezil (Type C)

20 g donepezil was weighed and placed in a 200 ml four-necked round bottom flask, and 120 ml methanol-denatured ethanol was added thereto. Then, the sample was dissolved by heating under stirring in a water bath at 50° C. After dissolved (44° C.), the solution was ice-cooled. Type-C seed crystals (100 mg) were added thereto at a bulk temperature of 30° C. After crystals were precipitated (a bulk temperature of 6.5° C.), the bulk temperature was raised to 20° C., and the mixture was stirred for 22 hours. Thereafter, it was ice-cooled again, and after stirred at a bulk temperature of 8° C. for 1 hour, the precipitated crystals were collected by filtration and washed with 12 ml methanol-denatured ethanol. The resulting crystals were dried for 2 hours with an air dryer at 50° C. to give 16.2 g of the title compound (yield, 81%).

By powder X-ray analysis, it was confirmed that the product was type C.

Example 13

Production of Crystal Polymorphism of Donepezil (Type C)

100 g donepezil was weighed and placed in a 1000 ml four-necked round bottom flask, and 600 ml methanol-denatured ethanol was added thereto. Then, the sample was dissolved by heating under stirring in a water bath at 50° C. After dissolved (45° C.), the solution was ice-cooled. Type-C seed crystals (500 mg) were added thereto at a bulk temperature of 30° C. After crystals were precipitated (a bulk temperature of 10° C.), the bulk temperature was raised to 25° C., and the mixture was stirred for 22 hours. Thereafter, it was ice-cooled again, and after stirred at a bulk temperature of 8° C. for 1 hour, the precipitated crystals were collected by filtration and washed with 60 ml methanol-denatured ethanol. The resulting crystals were dried for 2 hours with an air dryer at 50° C. to give 88.5 g of the title compound (yield, 88.5%).

By powder X-ray analysis, it was confirmed that the product was type C.

Example 14

Production of Crystal Polymorphism of Donepezil (Type C)

10 g donepezil was weighed and placed in a 100 ml four-necked round bottom flask, and 60 ml methanol-denatured ethanol and type-C seed crystals (50 mg) were added thereto and stirred (in the state of a suspension) for 8 hours under heating at 25° C. in a water bath. Thereafter, it was ice-cooled for 1 hour, and then the precipitated crystals were collected by filtration and washed with 6 ml methanol-denatured ethanol. The resulting crystals were dried for 3 hours with an air dryer at 50° C. to give the title compound.

By powder X-ray analysis, it was confirmed that the product was type C.

Example 15

Production of Crystal Polymorphism of Donepezil (Type C)

10 g type B donepezil was weighed and placed in a 100 ml four-necked round bottom flask, and 60 ml methanol-denatured ethanol and type-C seed crystals (50 mg) were added thereto and heated under stirring (in the state of a suspension) for 24 hours at 30° C. in a water bath. Thereafter, it was ice-cooled for 1 hour, and then the precipitated crystals were collected by filtration and washed with 6 ml methanol-denatured ethanol. The resulting crystals were dried for 3 hours with an air dryer at 50° C. to give 7.0 g of the title compound (yield, 70%).

By powder X-ray analysis, it was confirmed that the product was type C.

Example 16

Production of Crystal Polymorphism of Donepezil (Type C)

10 g type B donepezil was weighed and placed in a 100 ml four-necked round bottom flask, and 60 ml methanol-denatured ethanol and type-C seed crystals (50 mg) were added thereto and heated under stirring (in the state of a suspension) for 24 hours at 35° C. in a water bath. Thereafter, it was ice-cooled for 1 hour, and then the precipitated crystals were collected by filtration and washed with 6 ml methanol-denatured ethanol. The resulting crystals were dried with an air dryer at 50° C. to give the title compound.

By powder X-ray analysis, it was confirmed that the product was type C.

Examples are continued below.

The purity by HPLC of each product in Examples was determined under the following conditions.

HPLC Conditions

Solid phase: Inertsil ODS-2, 4.6$\phi$×15 cm

Mobile phase: water:acetonitrile:70% perchloric acid= 700:300:1

Flow rate: 0.8 ml/min.

Column temperature: 35° C.

Injection volume: 5$\mu$l

Detector: UV 271 nm

Example 17

Production of Crystal Polymorphism of Donepezil (Type C)

10 g crude donepezil concentrate obtained according to Examples 3 and 4 in JP-A 64-79151 was placed in a 100 ml four-necked round bottom flask, and 60 ml methanol-denatured ethanol was added thereto, and the sample was dissolved by heating at 50° C. After the dissolution of the sample was confirmed, the solution was cooled in an ice-cold water bath, and the precipitated dry crystals were collected by filtration and washed with 5 ml methanol-denatured ethanol. The resulting crystals were dried at 50° C. to give 6.5 g of the title compound (yield, 65.0%).

By powder X-ray analysis, it was confirmed that the product was type A.

Purity by HPLC (relative area method): 99.87%

Example 18

Production of Crystal Polymorphism of Donepezil (Type B)

10 g crude donepezil concentrate was placed in a 100 ml four-necked round bottom flask, and 60 ml methanol-denatured ethanol was added thereto, and the sample was dissolved by heating at 50° C. After the dissolution of the sample was confirmed, the solution was cooled in an ice-cold water bath, and when the bulk temperature was 30° C., type-B seed crystals were added thereto. The mixture was continued to be cooled as it was, and the precipitated dry crystals were collected by filtration and washed with 5 ml methanol-denatured ethanol. The resulting crystals were dried at 50° C. to give 7.2 g of the title compound (yield, 72.0%).

By powder X-ray analysis, it was confirmed that the product was type B.

Purity by HPLC (relative area method): 99.83%

Example 19

Production of Crystal Polymorphism of Donepezil (Type C)

10 g crude donepezil concentrate was placed in a 100 ml four-necked round bottom flask, and 60 ml methanol-denatured ethanol was added thereto, and the sample was dissolved by heating at 50° C. After the dissolution of the sample was confirmed, the solution was cooled in an ice-cold water bath, and when the bulk temperature was 27° C., type-C seed crystals were added thereto. The mixture was stirred for 4 hours as it was in warm water. The precipitated very dry crystals were collected by filtration and washed with 5 ml methanol-denatured ethanol. The resulting crystals were dried at 50° C. to give 7.4 g of the title compound (yield, 74.0%).

By powder X-ray analysis, it was confirmed that the product was type C.

Purity by HPLC (relative area method): 99.91%

Example 20

Production of Crystal Polymorphism of Donepezil (Type C)

10 g crude donepezil concentrate was placed in a 200 ml four-necked round bottom flask, and 60 ml methanol was added thereto, and the sample was dissolved by heating at 50° C. After the dissolution of the sample was confirmed, the solution was cooled in an ice-cold water bath, and when the bulk temperature was 30° C., type-C seed crystals were added thereto. The mixture was stirred for 4 hours as it was in warm water (29° C.) and then cooled in an ice-cold water bath. The precipitated crystals were collected by filtration and washed with 5 ml methanol. The resulting crystals were dried at 50° C. to give 6.65 g of the title compound (yield, 66.5%).

By powder X-ray analysis, it was confirmed that the product was type C.

Example 21

Production of Crystal Polymorphism of Donepezil (Type C)

10 g crude donepezil concentrate was placed in a 200 ml four-necked round bottom flask, and 60 ml ethanol was added thereto, and the sample was dissolved by heating at 50° C. After the dissolution of the sample was confirmed, the solution was cooled in an ice-cold water bath, and when the bulk temperature was 30° C., type-C seed crystals were added thereto. The mixture was stirred for 5 hours as it was in warm water (29° C.), and then cooled in an ice-cold water bath. The precipitated crystals were collected by filtration and washed with 5 ml methanol. The resulting crystals were dried at 50° C. to give 8.32 g of the title compound (yield, 83.2%).

By powder X-ray analysis, it was confirmed that the product was type C.

Example 22

Production of Crystal Polymorphism of Donepezil (Type C)

10 g crude donepezil concentrate was placed in a 100 ml four-necked round bottom flask, and 100 ml isopropyl alcohol (IPA) was added thereto, and the sample was dissolved by heating at 60° C. After the dissolution of the sample was confirmed, the solution was cooled in an ice-cold water bath, and when the bulk temperature was 37° C., type-C seed crystals were added thereto. The mixture was stirred for 5 hours as it was at a constant temperature (30 to 35° C.). Then, it was cooled in an ice cold water bath and the precipitated crystals were collected by filtration and washed with 5 ml IPA. The resulting crystals were dried at 50° C. to give 8.31 g of the title compound (yield, 83.1%).

By powder X-ray analysis, it was confirmed that the product was type C.

Example 23

Production of Crystal Polymorphism of Donepezil (Type C)

10 g crude donepezil concentrate was placed in a 50 ml four-necked round bottom flask, and 30 ml acetone was added thereto, and the sample was dissolved by heating at 50° C. After the dissolution of the sample was confirmed, the solution was cooled in an ice-cold water bath, and when the bulk temperature was 21° C., type-C seed crystals were added thereto. The mixture was stirred as it was for 0.5 hour at a constant temperature (24 to 25° C.). Then, it was cooled in an ice-cold water bath, and the precipitated crystals were collected by filtration and washed with 5 ml cold acetone. The resulting crystals were dried at 50° C. to give 6.03 g of the title compound (yield, 60.3%).

By powder X-ray analysis, it was confirmed that the product was type C.

Example 24

Production of Crystal Polymorphism of Donepezil (Type C)

10 g crude donepezil concentrate was placed in a 50 ml four-necked round bottom flask, and 30 ml methyl ethyl ketone (MEK) was added thereto, and the sample was dissolved by heating at 50° C. After the dissolution of the sample was confirmed, the solution was cooled in an ice-cold water bath, and when the bulk temperature was 15° C., type-C seed crystals were added thereto. The mixture was stirred as it was for 3 hours at a constant temperature (15 to 20° C.). Then, it was cooled in an ice-cold water bath, and the precipitated crystals were collected by filtration and washed with 5 ml MEK. The resulting crystals were dried at 50° C. to give 4.4 g of the title compound (yield, 44.0%).

By powder X-ray analysis, it was confirmed that the product was type C.

Example 25

Production of Crystal Polymorphism of Donepezil (Type C)

10 g crude donepezil concentrate was placed in a 50 ml four-necked round bottom flask, and 30 ml methyl isobutyl ketone (MIBK) was added thereto, and the sample was dissolved by heating at 50° C. After the dissolution of the sample was confirmed, the solution was cooled in an ice-cold water bath, and when the bulk temperature was 30° C., type-C seed crystals were added thereto. The mixture was stirred as it was for 1.5 hours at a constant temperature (22 to 30° C.). Then, it was cooled in an ice-cold water bath, and the precipitated crystals were collected by filtration and washed with 5 ml MIBK. The resulting crystals were dried at 50° C. to give 6.0 g of the title compound (yield, 60.0%).

By powder X-ray analysis, it was confirmed that the product was type C.

Example 26

Production of Crystal Polymorphism of Donepezil (Type C)

10 g crude donepezil concentrate was placed in a 200 ml four-necked round bottom flask, and 30 ml toluene-denatured ethanol was added thereto, and the sample was dissolved by heating at 50° C. After the dissolution of the sample was confirmed, the solution was cooled in an ice-cold water bath, and when the bulk temperature was 30° C., type-C seed crystals were added thereto. The mixture was stirred as it was for 5 hours in warm water (29° C.). Then, it was cooled in an ice-cold water bath, and the precipitated crystals were collected by filtration and washed with 5 ml toluene-denatured ethanol. The resulting crystals were dried at 50° C. to give 7.88 g of the title compound (yield, 78.8%).

By powder X-ray analysis, it was confirmed that the product was type C.

Example 27

Production of Crystal Polymorphism of Donepezil (Type C)

10 g crude donepezil concentrate was placed in a 100 ml four-necked round bottom flask, and 60 ml toluene-denatured ethanol was added thereto, and the sample was dissolved by heating at 50° C. After the dissolution of the sample was confirmed, the solution was cooled in an ice-cold water bath, and when the bulk temperature was 30° C., type-C seed crystals were added thereto. The mixture was stirred as it was for 4 hours in warm water (30° C.) and then cooled in an ice-cold water bath. The precipitated crystals were collected by filtration and washed with 5 ml toluene-denatured ethanol. The resulting crystals were dried at 50° C. to give 7.5 g of the title compound (yield, 75.0%).

By powder X-ray analysis, it was confirmed that the product was type C.

Example 28

Production of Crystal Polymorphism of Donepezil (Type C)

10 g crude donepezil concentrate was placed in a 50 ml four-necked round bottom flask, and 30 ml 2-methoxyethanol was added thereto, and the sample was dissolved by heating at 50° C. After the dissolution of the sample was confirmed, the solution was cooled in an ice-cold water bath, and when the internal temperature was 30° C., type-C seed crystals were added thereto. The mixture was stirred as it was for 5 hours in warm water (29° C.) and then cooled in an ice-cold water bath. The precipitated crystals were collected by filtration and washed with 5 ml 2-methoxyethanol. The resulting crystals were dried at 50° C. to give 5.97 g of the title compound (yield, 59.7%).

By powder X-ray analysis, it was confirmed that the product was type C.

Example 29

Production of Crystal Polymorphism of Donepezil (Type C)

10 g crude donepezil concentrate was placed in a 30 ml four-necked round bottom flask, and 10 ml THF was added thereto, and the sample was dissolved by heating at 50° C. After the dissolution of the sample was confirmed, the solution was cooled in an ice-cold water bath, and when the bulk temperature was 30° C., type-C seed crystals were added thereto. The mixture was stirred as it was for 6 hours in an ice-cold water bath, and the precipitated crystals were collected by filtration and washed with 5 ml THF. The resulting crystals were dried at 50° C. to give 3.11 g of the title compound (yield, 31.1%).

By powder X-ray analysis, it was confirmed that the product was type C.

Example 30

Production of Crystal Polymorphism of Donepezil 10 g crude donepezil concentrate was placed in a 50 ml four-necked round bottom flask, and 30 ml 1,4-dioxane was added thereto, and the sample was dissolved by heating at 50° C. After the dissolution of the sample was confirmed, the solution was cooled in an ice-cold water bath, and when the bulk temperature was 30° C., type-C seed crystals were added thereto. The mixture was stirred as it was for 7 hours at a constant temperature (23 to 25° C.) and then cooled in an ice-cold water bath. The precipitated crystals were collected by filtration and washed with 5 ml 1,4-dioxane. The resulting crystals were dried at 50° C. to give 6.2 g of the title compound (yield, 62.0%).

By powder X-ray analysis, it was confirmed that the product was type C.

Example 31

Production of Crystal Polymorphism of Donepezil (Type C)

10 g crude donepezil concentrate was placed in a 30 ml four-necked round bottom flask, and 10 ml 1,3-dioxorane was added thereto, and the sample was dissolved by heating at 50° C. After the dissolution of the sample was confirmed, the solution was cooled in an ice-cold water bath, and when the bulk temperature was 10° C., type-C seed crystals were added thereto. The mixture was stirred as it was for 1 hour in an ice-cold water bath, and the precipitated crystals were collected by filtration and washed with 5 ml 1,3-dioxorane. The resulting crystals were dried at 50° C. to give 2.92 g of the title compound (yield, 29.2%).

By powder X-ray analysis, it was confirmed that the product was type C.

Example 32

Production of Crystal Polymorphism of Donepezil (Type C)

10 g crude donepezil concentrate was placed in a 200 ml four-necked round bottom flask, and 30 ml 1,2-dimethoxyethane was added thereto, and the sample was dissolved by heating at 50° C. After the dissolution of the sample was confirmed, the solution was cooled in an ice-cold water bath, and when the bulk temperature was 30° C., type-C seed crystals were added thereto. The mixture was stirred as it was for 1.5 hours in an ice-cold water bath, and the precipitated crystals were collected by filtration and washed with 5 ml 1,2-dimethoxyethane. The resulting crystals were dried at 50° C. to give 4.26 g of the title compound (yield, 42.6%).

By powder X-ray analysis, it was confirmed that the product was type C.

Example 33

Production of Crystal Polymorphism of Donepezil (Type C)

10 g crude donepezil concentrate was placed in a 50 ml four-necked round bottom flask, and 30 ml methyl acetate was added thereto, and the sample was dissolved by heating at 50° C. After the dissolution of the sample was confirmed, the solution was cooled in an ice-cold water bath, and when the bulk temperature was 30° C., type-C seed crystals were added thereto. Thereafter, the mixture was stirred for 0.5 hour in an ice-cold water bath, and the precipitated crystals were collected by filtration and washed with 5 ml methyl acetate. The resulting crystals were dried at 50° C. to give 4.63 g of the title compound (yield, 46.3%).

By powder X-ray analysis, it was confirmed that the product was type C.

Example 34

Production of Crystal Polymorphism of Donepezil (Type C)

10 g crude donepezil concentrate was placed in a 200 ml four-necked round bottom flask, and 60 ml ethyl acetate was added thereto, and the sample was dissolved by heating at 50° C. After the dissolution of the sample was confirmed, the solution was cooled in an ice-cold water bath, and when the bulk temperature was 29° C., type-C seed crystals were added thereto. The precipitated crystals were stirred for 5 hours in warm water (30° C.) and then cooled in an ice-cold water bath. The precipitated crystals were collected by filtration and washed with 5 ml ethyl acetate. The resulting crystals were dried at 50° C. to give 1.29 g of the title compound (yield, 12.9%).

By powder X-ray analysis, it was confirmed that the product was type C.

Example 35

Production of Crystal Polymorphism of Donepezil (Type C)

10 g crude donepezil concentrate was placed in a 100 ml four-necked round bottom flask, and 30 ml ethyl acetate was added thereto, and the sample was dissolved by heating at 50° C. After the dissolution of the sample was confirmed, the solution was cooled in an ice-cold water bath, and when the bulk temperature was 30° C., type-C seed crystals were added thereto. The mixture was stirred for 5 hours in warm water (30° C.) and then cooled in an ice-cold water bath. The precipitated crystals were collected by filtration and washed with 5 ml ethyl acetate. The resulting crystals were dried at 50° C. to give 6.98 g of the title compound (yield, 69.8%).

By powder X-ray analysis, it was confirmed that the product was type C.

Example 36

Production of Crystal Polymorphism of Donepezil (Type C)

10 g crude donepezil concentrate was placed in a 50 ml four-necked round bottom flask, and 30 ml isopropyl acetate was added thereto, and the sample was dissolved by heating at 50° C. After the dissolution of the sample was confirmed, the solution was cooled in an ice-cold water bath, and when the bulk temperature was 30° C., type-C seed crystals were added thereto. The mixture was stirred as it was for 17 hours in warm water (29° C.) and then cooled in an ice-cold water bath. The precipitated crystals were collected by filtration and washed with 5 ml isopropyl acetate. The resulting crystals were dried at 50° C. to give 7.16 g of the title compound (yield, 71.6%) By powder X-ray analysis, it was confirmed that the product was type C.

Example 37

Production of Crystal Polymorphism of Donepezil (Type C)

10 g crude donepezil concentrate was placed in a 100 ml four-necked round bottom flask, and 60ml acetonitrile was added thereto, and the sample was dissolved by heating at 50° C. After the dissolution of the sample was confirmed, the solution was cooled in an ice-cold water bath, and when the bulk temperature was 30° C., type-C seed crystals were added thereto. The mixture was stirred as it was for 0.5 hour in an ice-cold water bath, and the precipitated crystals were collected by filtration and washed with 5 ml acetonitrile. The resulting crystals were dried at 50° C. to give 7.08 g of the title compound (yield, 70.8%).

By powder X-ray analysis, it was confirmed that the product was type C.

Example 38

Production of Crystal Polymorphism of Donepezil (Type C)

10 g crude donepezil concentrate was placed in a 50 ml four-necked round bottom flask, and 30 ml ethyl benzene was added thereto, and the sample was dissolved by heating at 50° C. After the dissolution of the sample was confirmed, the solution was cooled in an ice-cold water bath, and when the bulk temperature was 30° C., type-C seed crystals were added thereto. The mixture was stirred as it was for 3 hours at a constant temperature (18 to 24° C.). Then, it was cooled in an ice-cold water bath, and the precipitated crystals were collected by filtration and washed with 5 ml ethyl benzene. The resulting crystals were dried at 50° C. to give 3.54 g of the title compound (yield, 35.4%).

By powder X-ray analysis, it was confirmed that the product was type C.

Example 39

Production of Crystal Polymorphism of Donepezil (Type C)

10 g crude donepezil concentrate was placed in a 300 ml four-necked round bottom flask, and 200 ml cyclohexane was added thereto, and the sample was dissolved by heating at 60° C. After the dissolution of the sample was confirmed, the solution was cooled in an ice-cold water bath, and when the bulk temperature was 35° C., type-C seed crystals were added thereto. The mixture was stirred as it was for 3 hours at a constant temperature (35 to 40° C.). Then, the precipitated crystals were collected by filtration and washed with 5 ml cyclohexane. The resulting crystals were dried at 50° C. to give 6.43 g of the title compound (yield, 64.3%).

By powder X-ray analysis, it was confirmed that the product was type C.

Example 40

Production of Crystal Polymorphism of Donepezil (Type C)

10 g crude donepezil concentrate was placed in a 300 ml four-necked round bottom flask, and 270 ml diethyl ether was added thereto, and the sample was dissolved by heating at 40° C. After the dissolution of the sample was confirmed, the solution was cooled in an ice-cold water bath, and when the bulk temperature was 30° C., type-C seed crystals were added thereto. The mixture was stirred as it was for 3 hours at a constant temperature (20 to 25° C.). Then, it was cooled in an ice-cold water bath, and the precipitated crystals were collected by filtration and washed with 5 ml diethyl ether. The resulting crystals were dried at 50° C. to give 4.12 g of the title compound (yield, 41.2%)

By powder X-ray analysis, it was confirmed that the product was type C.

Example 41

Production of Crystal Polymorphism of Donepezil (Type C)

10 g crude donepezil concentrate was placed in a 200 ml four-necked round bottom flask, and 80 ml methanol and 30 ml water were added thereto, and the sample was dissolved by heating at 60° C. After the dissolution of the sample was confirmed, the solution was cooled in an ice-cold water bath, and when the bulk temperature was 30° C., type-C seed crystals were added thereto. The mixture was stirred as it was for 6 hours at a constant temperature (20 to 30° C.). Then, it was cooled in an ice-cold water bath, and the precipitated crystals were collected by filtration and washed with 5 ml cold methanol. The resulting crystals were dried at 50° C. to give 7.23 g of the title compound (yield, 72.3%).

By powder X-ray analysis, it was confirmed that the product was type C.

Example 42

Production of Crystal Polymorphism of Donepezil (Type C)

10 g crude donepezil concentrate was placed in a 100 ml four-necked round bottom flask, and 50 ml acetonitrile and 30 ml water were added thereto, and the sample was dissolved by heating at 50° C. After the dissolution of the sample was confirmed, the solution was cooled in an ice-cold water bath, and when the bulk temperature was 32° C., type-C seed crystals were added thereto. The mixture was cooled as it was in an ice-cold water bath, and the precipitated crystals were collected by filtration and washed with 5 ml cold acetonitrile. The resulting crystals were dried at 50° C. to give 9.1 g of the title compound (yield, 91.0%)

By powder X-ray analysis, it was confirmed that the product was type C.

Example 43

Production of Crystal Polymorphism of Donepezil (Type C)

10 g crude donepezil concentrate was placed in a 100 ml four-necked round bottom flask, and 70 ml acetonitrile and 50 ml water were added thereto, and the sample was dissolved by heating at 50° C. After the dissolution of the sample, the solution was cooled in an ice-cold water bath, and when the bulk temperature was 28° C., type-C seed crystals were added thereto. The mixture was cooled as it was in an ice-cold water bath, and the precipitated crystals were collected by filtration and washed with 5 ml cold acetonitrile. The resulting crystals were dried at 50° C. to give 8.5 g of the title compound (yield, 85.0%).

By powder X-ray analysis, it was confirmed that the product was type C.

Example 44

Production of Crystal Polymorphism of Donepezil (Type C)

10 g crude donepezil concentrate was placed in a 100 ml four-necked round bottom flask, and 30 ml acetonitrile and 30 ml hexane were added thereto, and the sample was dissolved by heating at 50° C. After the dissolution of the sample was confirmed, the solution was cooled in an ice-cold water bath, and when the bulk temperature was 13° C., type-C seed crystals were added thereto. The mixture was stirred for 0.5 hour at a constant temperature (18 to 19° C.). Then, it was cooled in an ice-cold water bath, and the precipitated crystals were collected by filtration and washed with 5 ml mixed solvent of acetone:hexane (1 : 1). The resulting crystals were dried at 50° C. to give 6.3 g of the title compound (yield, 63.0%).

By powder X-ray analysis, it was confirmed that the product was type C.

Comparative Examples 1 to 3

Production of Donepezil

Donepezil was produced according to Examples 3 and 4 of JP-A 64-79151 and purified by column chromatography under the following conditions.

Comparative Example 1

Production of Donepezil (Purification by Column Chromatography)

Reduction reaction was carried out according to Example 4 in JP-A 64-79151. After the reaction was completed, the resulting solution in THF was concentrated to give 5.0 g crude donepezil. This product was dissolved in 50 ml methylene chloride and adsorbed onto a chromatographic column packed with 250 g silica gel (Wako Gel C-200™) and eluted with 3000 ml of methylene chloride:methanol (50:1).

The eluate was evaporated in a warm water bath at 50° C. to give 4.6 g of the title compound (yield, 92%).

Purity by HPLC (relative area method): 99.92%

Comparative Example 2

Production of Donepezil (Purification by Column Chromatography)

The sample was eluted with 2000 ml of 1% methanol/methylene chloride and then with 1000 ml of 2% methanol/methylene chloride in the same manner as in Comparative Example 1.

The eluate was evaporated in a warm water bath at 50° C. to give 4.4 g of the title compound (yield, 88%). Purity by HPLC (relative area method): 99.90%

Comparative Example 3

Production of Donepezil (Purification by Column Chromatography)

Reduction reaction was carried out according to Example 4 in JP-A 64-79151. After the reaction was completed, the resulting solution in THF was concentrated to give 300 mg crude donepezil. This product was dissolved in 3 ml methylene chloride and adsorbed onto a chromatographic column packed with 3 g silica gel (Wako Gel C-200™) and eluted with 50 ml of methylene chloride:methanol (50:1).

The eluate was evaporated in a warm water bath at 50° C. to give 200 mg of the title compound (yield, 66.7%).

Purity by HPLC (relative area method): 99.82%

Comparison of Residual Solvents

Then, the residuals solvents in donepezil of the present invention (type (A) to (C)) and in donepezil produced according to the prior art were measured using a capillary column according to the Japanese Pharmacopoeia, general test methods, gas chromatography. The results are shown below.

| Type | Example | Residual Solvent | |
|---|---|---|---|
| Type (A) | 17 | ethanol | 51 ppm |
| Type (B) | 18 | ethanol | 222 ppm |
| Type (C) | 19 | ethanol | 96 ppm |
| Prior Art | Comparative Example 3 | methylene chloride | 2300 ppm |

As a result of re-measurement, the polymorphic crystals (A) to (C) according to the present invention are also novel polymorphic crystals which are also characterized by the following peaks in its powder X-ray diffraction pattern.

(1) Type A Crystals (Example 17)

Figure 10:
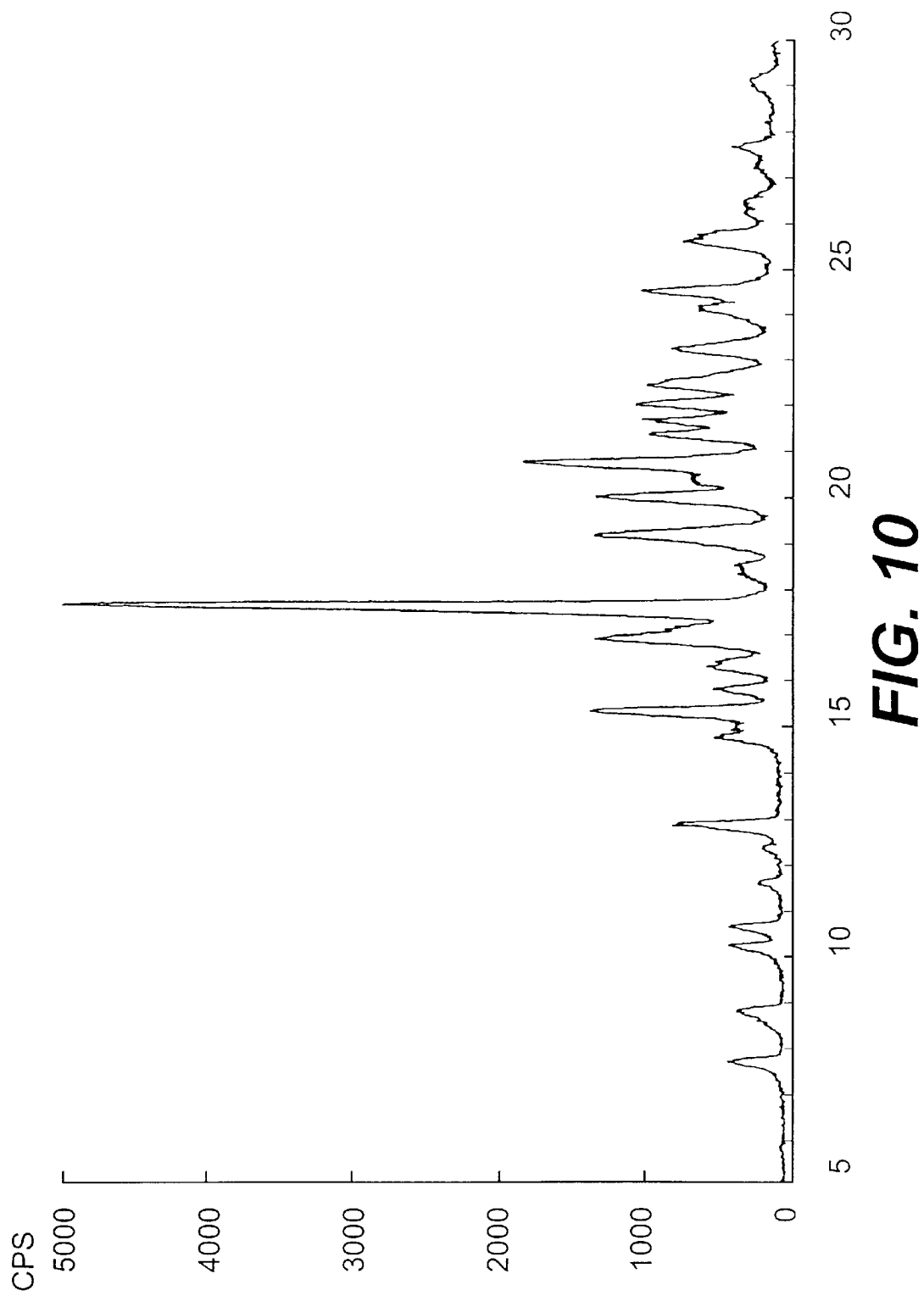
FIG. 10 shows a powder X-ray diffraction pattern of type A donepezil crystals.

Peaks in powder X-ray diffraction pattern (see FIG. 10):

| Diffraction angle (2θ, °) | Intensity (I/I₀) |
|---|---|
| 7.64 | 8 |
| 8.42 | 2 |
| 8.74 | 7 |
| 10.14 | 7 |
| 10.58 | 7 |
| 11.56 | 3 |
| 12.30 | 2 |
| 12.82 | 15 |
| 14.74 | 8 |
| 15.30 | 27 |
| 15.78 | 8 |
| 16.30 | 8 |
| 16.90 | 24 |
| 17.60 | 100 |
| 18.36 | 3 |
| 18.54 | 3 |
| 19.22 | 24 |
| 20.04 | 23 |
| 20.40 | 9 |
| 20.76 | 33 |
| 21.42 | 15 |
| 21.70 | 14 |
| 22.10 | 17 |
| 22.54 | 15 |
| 23.32 | 12 |
| 24.22 | 9 |
| 24.62 | 16 |
| 25.72 | 11 |
| 26.32 | 3 |
| 26.52 | 3 |
| 27.34 | 2 |
| 27.72 | 5 |
| 29.12 | 3 |

(2) Type B Crystals (Example 18)

Figure 11:
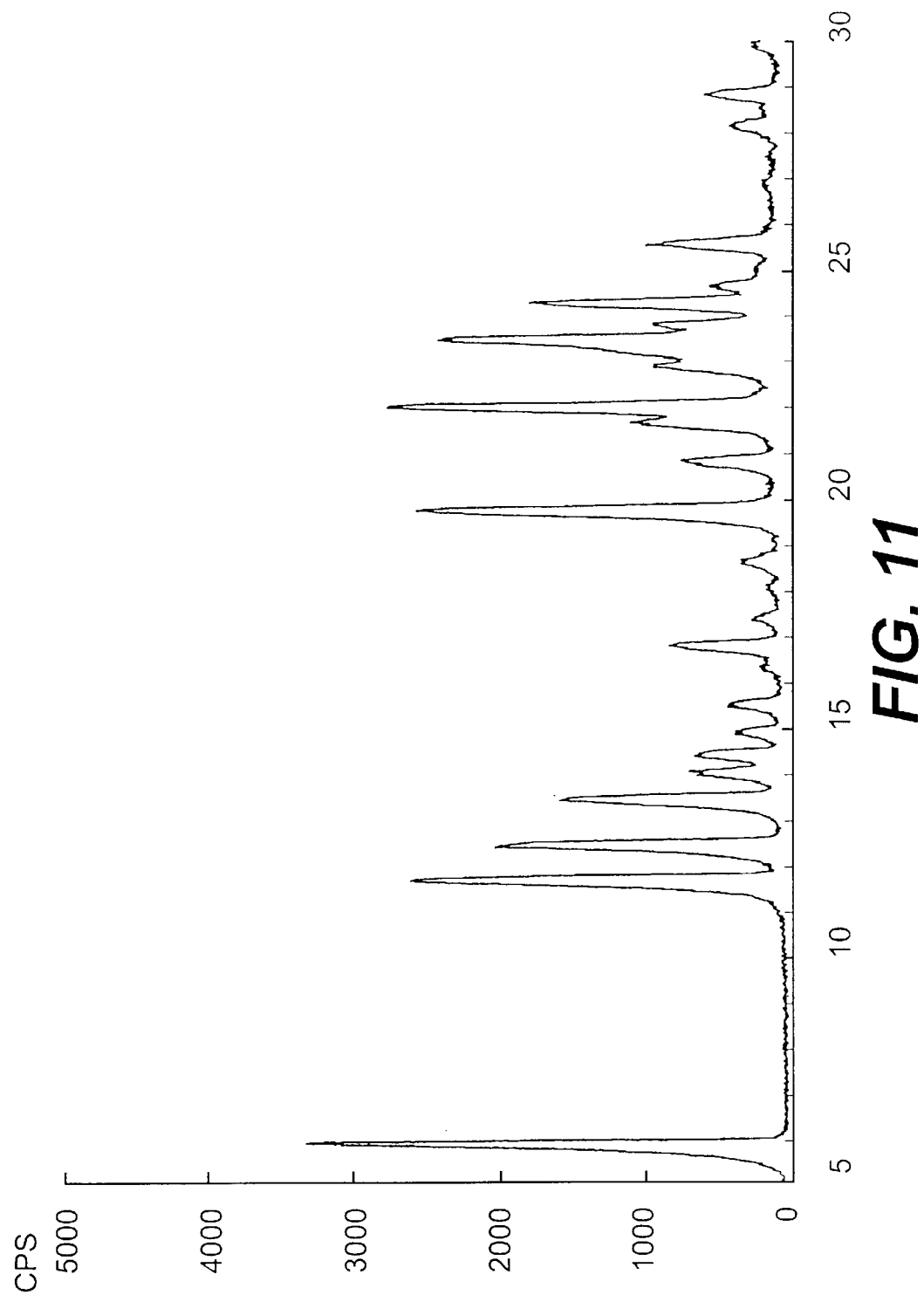
FIG. 11 shows a powder X-ray diffraction pattern of type B donepezil crystals.

Peaks in powder X-ray diffraction pattern (see FIG. 11):

| Diffraction angle (2θ, °) | Intensity (I/I₀) |
|---|---|
| 5.82 | 95 |
| 11.54 | 96 |
| 12.30 | 74 |
| 13.32 | 56 |
| 13.92 | 22 |
| 14.32 | 22 |
| 14.82 | 11 |
| 15.44 | 13 |
| 16.26 | 3 |
| 16.72 | 28 |
| 17.34 | 5 |
| 18.58 | 8 |
| 19.70 | 90 |
| 20.78 | 22 |
| 21.64 | 34 |
| 21.98 | 100 |
| 22.88 | 29 |
| 23.48 | 85 |
| 23.80 | 29 |
| 24.28 | 61 |
| 24.68 | 15 |
| 25.08 | 4 |
| 25.58 | 29 |
| 26.92 | 2 |
| 28.12 | 11 |
| 28.82 | 17 |

(3) Type C Crystals (Example 19)

Figure 12:
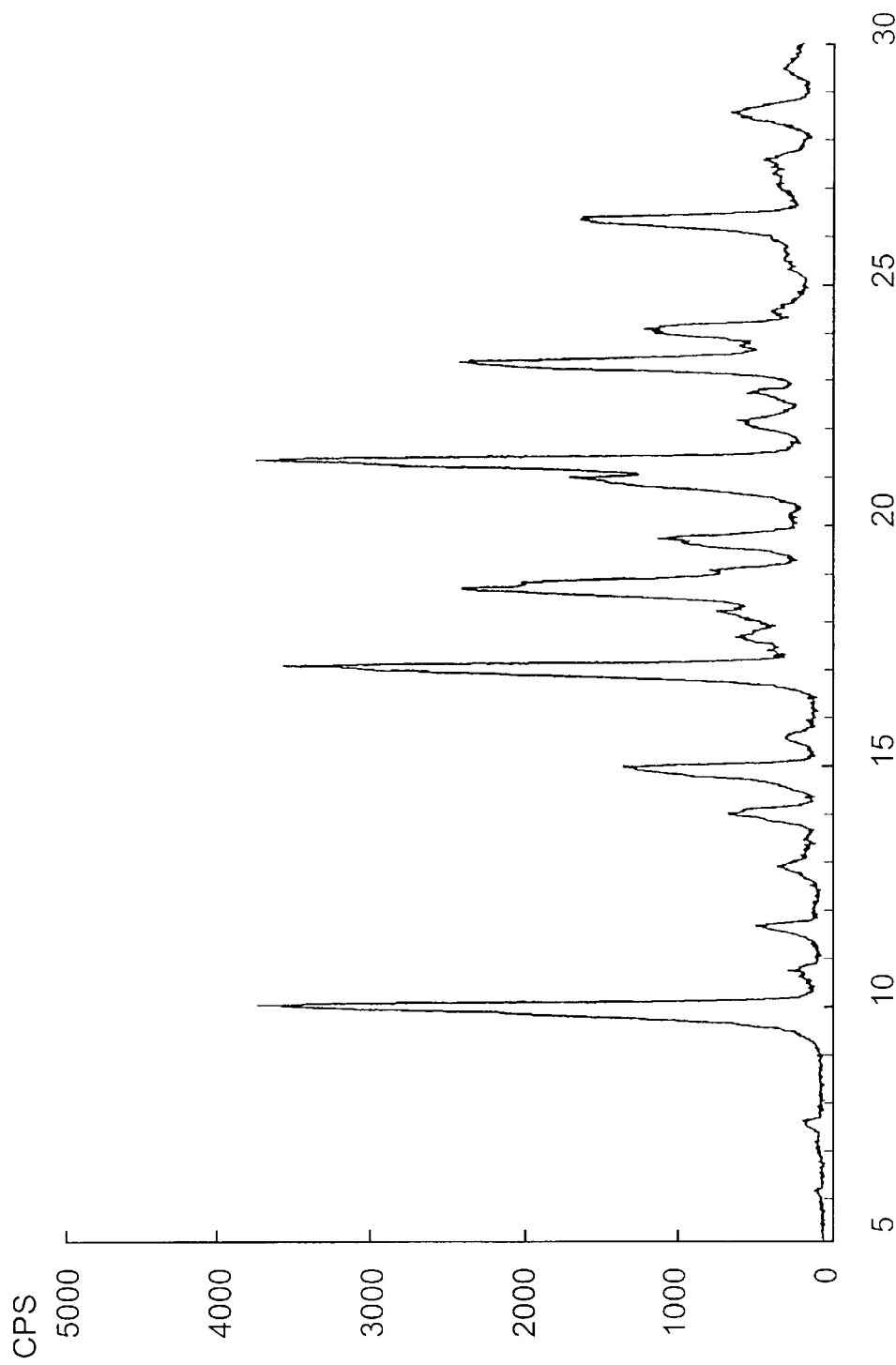
FIG. 12 shows a powder X-ray diffraction pattern of type C donepezil crystals.

Peaks in powder X-ray diffraction pattern (see FIG. 12):

| Diffraction angle (2θ, °) | Intensity (I/I₀) |
|---|---|
| 6.06 | 1 |
| 7.10 | 1 |
| 7.48 | 3 |
| 9.86 | 100 |
| 10.52 | 3 |
| 10.68 | 4 |
| 11.56 | 11 |
| 12.78 | 6 |
| 13.42 | 2 |
| 13.94 | 15 |
| 14.86 | 34 |
| 15.56 | 5 |
| 16.98 | 91 |
| 17.64 | 12 |
| 18.16 | 15 |
| 18.64 | 61 |
| 19.08 | 15 |
| 19.70 | 25 |
| 20.22 | 2 |
| 20.94 | 40 |
| 21.34 | 95 |
| 22.16 | 10 |
| 22.78 | 8 |
| 23.38 | 62 |
| 24.12 | 28 |
| 24.50 | 5 |
| 25.64 | 3 |
| 26.36 | 41 |
| 27.10 | 4 |
| 27.36 | 4 |
| 27.60 | 6 |
| 28.56 | 12 |
| 29.48 | 3 |

What is claimed is:

1. A polymorphic crystal (A) of donepezil represented by the following formula:

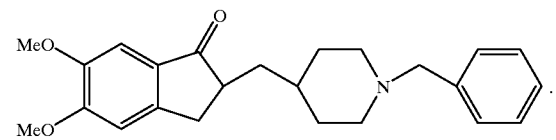

characterized by having peaks at the following diffraction angles (2θ) in its powder X-ray diffraction pattern;

| Diffraction angle (2θ, °) | Intensity (I/I₀) |
|---|---|
| 7.68 | 8 |
| 8.52 | 4 |
| 8.80 | 7 |
| 10.20 | 8 |
| 10.64 | 8 |
| 11.60 | 5 |
| 12.86 | 16 |
| 14.80 | 12 |
| 15.34 | 30 |
| 15.82 | 8 |
| 16.34 | 10 |
| 16.96 | 22 |
| 17.66 | 100 |
| 19.26 | 24 |
| 20.08 | 29 |
| 20.46 | 17 |
| 20.82 | 35 |
| 21.46 | 17 |
| 21.76 | 17 |

-continued

| Diffraction angle (2θ, °) | Intensity (I/I$_O$) |
|---|---|
| 22.14 | 21 |
| 22.60 | 21 |
| 23.38 | 20 |
| 24.28 | 14 |
| 24.66 | 19 |
| 25.78 | 16 | and/or peaks at the following wavelengths in its infrared absorption spectrum in potassium bromide: 561.3, 699.8, 743.1, 803.1, 841.3, 858.4, 893.8, 972.5, 1035.7, 1074.7, 1122.9, 1191.8, 1220.3, 1262.4, 1311.8, 1365.6, 1420.5, 1456.6, 1501.3, 1589.0, 1690.1, 2799.6, 2919.1 cm$^{-1}$.

2. A polymorphic crystal (B) of donepezil, characterized by having peaks at the following diffraction angles (2θ) in its powder X-ray diffraction pattern;

| Diffraction angle (2θ, °) | Intensity (I/I$_O$) |
|---|---|
| 5.82 | 79 |
| 11.28 | 8 |
| 11.46 | 26 |
| 11.58 | 60 |
| 11.86 | 5 |
| 12.04 | 10 |
| 12.30 | 36 |
| 13.02 | 17 |
| 13.30 | 38 |
| 13.66 | 7 |
| 13.88 | 11 |
| 14.40 | 6 |
| 15.34 | 8 |
| 15.46 | 10 |
| 16.46 | 9 |
| 16.60 | 14 |
| 16.74 | 13 |
| 18.00 | 11 |
| 18.30 | 8 |
| 18.56 | 9 |
| 19.34 | 12 |
| 19.48 | 26 |
| 19.70 | 42 |
| 20.24 | 9 |
| 20.76 | 15 |
| 21.34 | 14 |
| 21.58 | 24 |
| 21.72 | 33 |
| 21.90 | 100 |
| 22.76 | 13 |
| 22.90 | 16 |
| 23.22 | 26 |
| 23.48 | 35 |
| 23.82 | 14 |
| 24.04 | 17 |
| 24.22 | 38 |
| 24.52 | 8 |
| 24.66 | 12 |
| 25.60 | 20 |
| 28.04 | 7 | and/or peaks at the following wavelengths in its infrared absorption spectrum in potassium bromide: 561.7, 697.5, 738.0, 770.0, 809.6, 861.9, 976.0, 1037.8, 1073.8, 1119.7, 1221.4, 1266.3, 1308.4, 1365.0, 1420.4, 1453.9, 1468.9, 1500.0, 1591.7, 1685.7, 2761.3, 2922.2, 3029.5, 3067.7 cm$^{-1}$.

3. A polymorphic crystal (C) of donepezil, characterized by having peaks at the following diffraction angles (2θθ) in its powder X-ray diffraction pattern;

| Diffraction angle (2θ, °) | Intensity (I/I$_O$) |
|---|---|
| 7.42 | 3 |
| 7.56 | 4 |
| 9.60 | 4 |
| 9.74 | 10 |
| 9.82 | 15 |
| 9.94 | 23 |
| 11.46 | 4 |
| 11.58 | 6 |
| 11.68 | 9 |
| 13.78 | 8 |
| 13.90 | 17 |
| 14.08 | 29 |
| 14.78 | 14 |
| 14.94 | 25 |
| 17.00 | 100 |
| 17.18 | 48 |
| 18.12 | 10 |
| 18.22 | 10 |
| 18.44 | 8 |
| 18.60 | 12 |
| 18.84 | 19 |
| 18.98 | 17 |
| 19.12 | 17 |
| 19.76 | 17 |
| 20.30 | 9 |
| 20.86 | 13 |
| 21.00 | 18 |
| 21.14 | 25 |
| 21.50 | 48 |
| 23.44 | 26 |
| 23.92 | 17 |
| 24.20 | 10 |
| 26.22 | 13 |
| 26.54 | 25 |
| 27.74 | 7 |
| 28.80 | 7 | and/or peaks at the following wavelengths in its infrared absorption spectrum in potassium bromide: 559.8, 648.4, 698.7, 733.5, 746.2, 768.1, 787.2, 818.8, 863.7, 974.0, 1036.4, 1073.0, 1122.1, 1221.3, 1263.0, 1310.3, 1342.3, 1367.5, 1438.1, 1459.1, 1498.6, 1591.9, 1688.1, 2909.3 cm$^{-1}$.

4. A process for producing polymorphic crystal (A) of donepezil, which comprises the step of crystallizing a solution of donepezil/methanol-denatured ethanol at 10° C. or less within 20 hours.

5. A process for producing polymorphic crystal (B) of donepezil, which comprises the step of concentrating a solution of donepezil/THF.

6. A process for producing polymorphic crystal (B) of donepezil, which comprises the step of crystallizing a solution of donepezil/methanol-denatured ethanol at 10° C. or less for 20 hours or more.

7. A process for producing polymorphic crystal (C) of donepezil, which comprises the steps of cooling a solution of donepezil/methanol-denatured ethanol at 10° C. or less, and after crystal precipitation, heating it at 20° C. or more after the precipitation of the crystals and further cooling it at 10° C. or less to crystallize.

8. A process for producing polymorphic crystal (C) of donepezil, which comprises the steps of cooling a solution of donepezil/methanol-denatured ethanol, and crystallizing it at 15 to 25° C. after the precipitation of the crystals.

9. A process for producing polymorphic crystal (C) of donepezil, which comprises the step of gradually cooling donepezil/methanol-denatured ethanol.

10. A process for producing polymorphic crystal (A) of donepezil, which comprises the steps of adding seed crystals of polymorphic crystal (A) to a solution of donepezil and crystallizing it at 20° C. or less within 1 hour.

11. A process for producing polymorphic crystal (B) of donepezil, which comprises the steps of adding seed crystals of polymorphic crystal (B) to a solution of donepezil, cooling it at 15° C. or less and then crystallizing it at 20 to 30° C. within 2 hours.

12. A process for producing polymorphic crystal (B) of donepezil, which comprises the steps of adding seed crystals of polymorphic crystal (B) to a solution of donepezil and crystallizing it at 15° C. or less within 1 hour.

13. A process for producing polymorphic crystal (C) of donepezil, which comprises the steps of adding seed crystals of polymorphic crystal (C) to a solution of donepezil, cooling it at 15° C. or less and then crystallizing it at 25 to 35° C. for 2 hours or more and further at 15° C. or less.

14. A process for producing polymorphic crystal (C) of donepezil, which comprises the step of suspending donepezil and seed crystals of polymorphic crystal (C) in a solvent at 20 to 40° C.

15. The process for producing polymorphic crystal (C) of donepezil as claimed in claim 14, wherein the solvent is a lower alcohol.

16. The process for producing polymorphic crystal (C) of donepezil as claimed in claim 15, wherein the lower alcohol is at least one selected from the group consisting of methanol, ethanol, n-propanol and i-propanol.

17. The process for producing polymorphic crystal (C) of donepezil as claimed in claim 14, wherein the solvent is methanol-denatured ethanol.

18. A process for producing polymorphic crystal (A) of donepezil, which comprises the steps of dissolving donepezil in methanol-denatured ethanol, and then adding type-A seed crystals to crystallize.

19. A process for producing polymorphic crystal (B) of donepezil, which comprises the steps of dissolving donepezil in methanol-denatured ethanol, and then adding type-B seed crystals to crystallize.

20. A process for producing polymorphic crystal (C) of donepezil, which comprises the steps of dissolving donepezil in methanol-denatured ethanol, and then adding type-C seed crystals to crystallize.

21. A process for producing polymorphic crystal (C) of donepezil, which comprises the steps of dissolving donepezil in at least one solvent selected from the group consisting of methanol, ethanol, isopropanol, acetone, methyl ethyl ketone, methyl isobutyl ketone, toluene-denatured ethanol, 2-ethoxyethanol, THF, 1,4-dioxane, 1,3-dioxolane, 1,2-dimethoxyethane, methyl acetate, ethyl acetate, isopropyl acetate, acetonitrile, ethyl benzene, cyclohexane, diethyl ether, diisopropyl ether, a mixed solvent of methanol/water, a mixed solvent of acetonitrile/water and a mixed solvent of acetone/hexane, and then adding type-C seed crystals to crystallize.

* * * * *